US012419819B2

(12) United States Patent
Fukuda

(10) Patent No.: US 12,419,819 B2
(45) Date of Patent: Sep. 23, 2025

(54) METHOD FOR FORMING COATING FILM

(71) Applicant: KAO CORPORATION, Tokyo (JP)

(72) Inventor: Teruyuki Fukuda, Wakayama (JP)

(73) Assignee: KAO CORPORATION, Tokyo (JP)

( * ) Notice: Subject to any disclaimer, the term of this patent is extended or adjusted under 35 U.S.C. 154(b) by 799 days.

(21) Appl. No.: 17/311,145

(22) PCT Filed: Nov. 22, 2019

(86) PCT No.: PCT/JP2019/045887
§ 371 (c)(1),
(2) Date: Jun. 4, 2021

(87) PCT Pub. No.: WO2020/116216
PCT Pub. Date: Jun. 11, 2020

(65) Prior Publication Data
US 2022/0023171 A1    Jan. 27, 2022

(30) Foreign Application Priority Data
Dec. 7, 2018    (JP) .................. 2018-230172

(51) Int. Cl.
| | |
|---|---|
| A61K 8/34 | (2006.01) |
| A61G 1/02 | (2006.01) |
| A61K 8/58 | (2006.01) |
| A61K 8/81 | (2006.01) |
| A61K 8/891 | (2006.01) |
| A61K 8/896 | (2006.01) |
| A61Q 1/02 | (2006.01) |
| B05D 1/02 | (2006.01) |

(52) U.S. Cl.
CPC ............ *A61K 8/34* (2013.01); *A61K 8/585* (2013.01); *A61K 8/8111* (2013.01); *A61K 8/8158* (2013.01); *A61K 8/891* (2013.01); *A61K 8/896* (2013.01); *A61Q 1/02* (2013.01); *B05D 1/02* (2013.01); *A61K 2800/43* (2013.01); *A61K 2800/5426* (2013.01); *A61K 2800/591* (2013.01)

(58) Field of Classification Search
CPC ........ A61K 8/34; A61K 8/585; A61K 8/8111; A61K 8/8158; A61K 8/891; A61K 8/896; A61K 2800/43; A61K 2800/5426; A61K 2800/591; A61Q 1/02; B05D 1/02
See application file for complete search history.

(56) References Cited

U.S. PATENT DOCUMENTS

| | | | |
|---|---|---|---|
| 6,214,319 B1 | 4/2001 | Franzke et al. | |
| 7,794,905 B2 | 9/2010 | De Jong et al. | |
| 2007/0258932 A1 | 11/2007 | Bui et al. | |
| 2013/0079368 A1 | 3/2013 | Omura et al. | |
| 2013/0280198 A1 | 10/2013 | Cavazutti et al. | |
| 2014/0212363 A1 | 7/2014 | Harman et al. | |
| 2014/0364394 A1* | 12/2014 | Tamura .............. | A61Q 5/10 556/456 |
| 2016/0051028 A1* | 2/2016 | Lahousse .......... | A61K 8/891 401/196 |
| 2018/0028430 A1* | 2/2018 | Aoshima ............ | A61K 8/91 |
| 2019/0343731 A1 | 11/2019 | Amari et al. | |
| 2021/0085592 A1 | 3/2021 | Nagai et al. | |

FOREIGN PATENT DOCUMENTS

| | | | | |
|---|---|---|---|---|
| CN | 101084864 A | 12/2007 | | |
| EP | 0 841 060 A2 | 5/1998 | | |
| EP | 3366271 A1 * | 8/2018 | ............ | A45D 34/04 |
| JP | 61-183208 A | 8/1986 | | |
| JP | 10-130302 A | 5/1998 | | |
| JP | 11-12303 A | 1/1999 | | |
| JP | 11-80201 A | 3/1999 | | |
| JP | 2004-269514 A | 9/2004 | | |
| JP | 2007-99785 A | 4/2007 | | |
| JP | 2008-242453 A | 10/2008 | | |
| JP | 2013-151660 A | 8/2013 | | |
| JP | 2014-70032 A | 4/2014 | | |
| JP | 2015-520120 A | 7/2015 | | |
| JP | 2016-519094 A | 6/2016 | | |
| JP | 2016-160205 A | 9/2016 | | |
| JP | 2017-39669 A | 2/2017 | | |
| JP | 2017-122076 A | 7/2017 | | |
| JP | 2017-538748 A | 12/2017 | | |
| WO | WO-2013036878 A1 * | 3/2013 | ............ | A61K 47/34 |
| WO | WO 2014/154698 A2 | 10/2014 | | |
| WO | WO-2017069080 A1 * | 4/2017 | ............ | A45D 34/04 |

(Continued)

OTHER PUBLICATIONS

Machine translation of WO-2017069080-A1 (Year: 2017).*
Alpha Chemistry; Homosalate; https://www.alfa-chemistry.com/product/homosalate-cas-118-56-9-44667.html (accessed Jan. 2024) (Year: 2024).*
Hansen Solubility Parameters; https://www.hansen-solubility.com/HSP-science/solvent-blends.php (accessed Jan. 2024) (Year: 2017).*
https://www.codinter.com/en/electrostatic-atomization-what-is-it-and-what-equipment-is-needed/#:~:text=Electrostatic%20atomization%20is%20an%20industrial,of%20the%20liquid%20is%20achieved. (accessed Jan. 2024) (Year: 2021).*

(Continued)

*Primary Examiner* — Robert A Wax
*Assistant Examiner* — John W Lippert, III
(74) *Attorney, Agent, or Firm* — Oblon, McClelland, Maier & Neustadt, L.L.P.

(57) ABSTRACT

The present invention relates to a method for forming a coating film including a step of coating a liquid composition I containing a solvent A, a solvent B, and a polymer C to skin, wherein a boiling point of the solvent A is lower than 99° C., and a distance Ra of the Hansen solubility parameter of the solvent A to water is 36 or less; a boiling point of the solvent B is 150° C. or higher, and a distance Ra of the Hansen solubility parameter of the solvent B to water is 40 or more; and the solvent B is compatible with the solvent A, and the polymer C is soluble in the solvent A but insoluble in the solvent B.

20 Claims, 5 Drawing Sheets

(56) References Cited

FOREIGN PATENT DOCUMENTS

WO    WO 2018/124227 A1    7/2018
WO    WO 2019/044327 A1    3/2019

OTHER PUBLICATIONS

Log P discussion; Fluconazole; Log P discussion; Dash et al.; Fluconazole; Academic Press; Analytical Profiles of Drug Substances and Excipients vol. 27 (Year: 2001).*
Log P and Ra values of different solvents (Year: 2024).*
Sodium carboxymethylcellulose; https://www.sigmaaldrich.com/US/en/product/aldrich/419338 (site accessed Jan. 2024) (Year: 2024).*
Extended European Search Report issued Aug. 9, 2022 in European Patent Application No. 19891815.3, 9 pages.
International Search Report issued on Feb. 4, 2020 in PCT/JP2019/045887 filed on Nov. 22, 2019, (3 pages).

* cited by examiner

METHOD FOR FORMING COATING FILM

FIELD OF THE INVENTION

The present invention relates to a method for forming a coating film.

BACKGROUND OF THE INVENTION

Conventionally, in cosmetics to be applied to the skin, there have been made attempts to scatter or reflect incident light on the skin by blending spherical or plate-like inorganic fine particles or the like, thereby adjusting the contract between dark areas of sulcus cutis or pores of the skin or the like and bright areas of crista cutis or the like and concealing unevenness of the skin, such as sulcus cutis or pores of the skin.

For example, JP 2015-520120 A (PTL 1) intends to decrease the skin imperfections, particularly the visibility of pores of the skin and make the pore hiding effect long lasting and describes, as a cosmetic method using a cosmetic composition used as a skin care or makeup base or primer, a cosmetic method including a step of applying a plate type filler having predetermined refractive index and particle diameter, a silicone elastomer, and a filler having an oil absorption capacity of 1 mL/g or more in a physiologically acceptable medium to the skin.

In addition, JP 2017-538748 A (PTL 2) describes, as a method for improving the appearance of the skin, a method including a step of applying a composition containing a thermoplastic elastomer, an adhesive polymer, a filler, and a pigment to the skin, to form a film on the skin.

SUMMARY OF THE INVENTION

The present invention relates to the following [1].

[1] A method for forming a coating film including a step of coating a liquid composition I containing a solvent A, a solvent B, and a polymer C to skin, wherein
a boiling point of the solvent A is lower than 99° C., and a distance Ra of the Hansen solubility parameter of the solvent A to water as expressed by the following equation (1) is 36 or less,
a boiling point of the solvent B is 150° C. or higher, and a distance Ra of the Hansen solubility parameter of the solvent B to water as expressed by the following equation (1) is 40 or more, and
the solvent B is compatible with the solvent A, and the polymer C is soluble in the solvent A but insoluble in the solvent B, $$Ra=(4\times\Delta D^2+\Delta P^2+\Delta H^2)^{0.5} \quad (1)$$

wherein,
ΔD is a difference of dispersing component in the Hansen solubility parameter between a solvent and water,
ΔP is a difference of polar component and water in the Hansen solubility parameter between a solvent, and
ΔH is a difference of hydrogen-binding component in the Hansen solubility parameter between a solvent and water.

DETAILED DESCRIPTION OF THE INVENTION

In the case of applying inorganic fine particles scatting or reflecting light in a liquid state, such as a liquid foundation, a lot of the inorganic fine particles flow into the sulcus cutis or pores of the skin and are unevenly distributed in the sulcus cutis or pores of the skin, thereby possibly making the sulcus cutis or pores of the skin rather noticeable.

In addition, the inorganic fine particles applied to the crista cutis come into the sulcus cutis or pores of the skin via, as a medium, sebum, sweat, or the like, which is secreted after putting on makeup, thereby possibly making the sulcus cutis or pores of the skin more noticeable. Such a phenomenon is conspicuously seen especially on a makeup coating film formed of a cosmetic containing a colored inorganic pigment, such as a metal oxide having a high refractive index.

Figure 1:
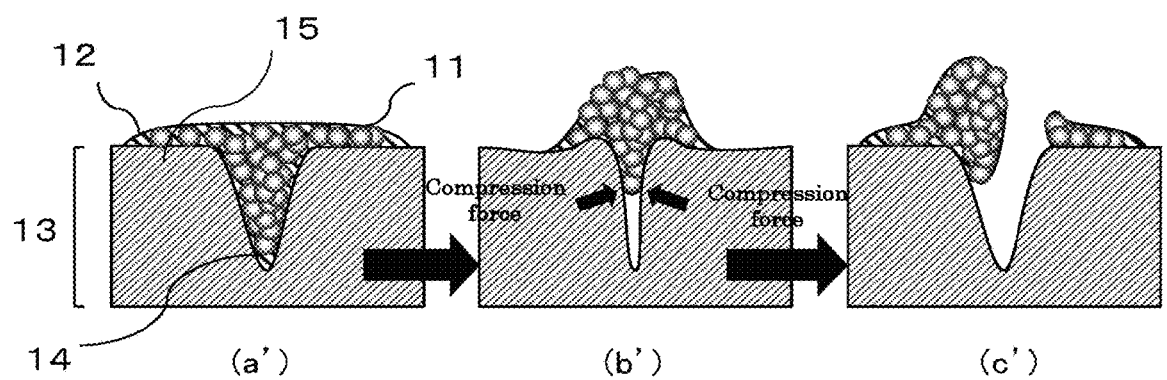
FIG. 1 is a schematic view showing a cross section of a coating film formed by coating a cosmetic containing inorganic fine particles on the skin.

Furthermore, in the case where deformations are brought on the sulcus cutis or wrinkles of the skin due to a change of facial expression or the like, the inorganic fine particles which have been taken into the inside of the sulcus cutis or wrinkles are pushed out onto the surface following a volume change of the sulcus cutis or wrinkles as shown in, for example, FIGS. 1(a') to 1(c'), resulting in generation of makeup deteriorations, such as twist or peeling of the coating film. Such makeup deterioration causes such problems that the finish immediately after putting on makeup cannot be kept, when the surface of the makeup coating film is scraped by clothes, fingers, or the like, cosmetic transfer is caused, and the applied makeup is further deteriorated, whereby the clothes, fingers, or the like are contaminated with the inorganic fine particles.

The present invention relates to a method for forming a coating film which is excellent in concealment of unevenness of the skin, hardly causes makeup deterioration, and is excellent in makeup durability.

The present inventor has found that in coating a liquid composition containing two kinds of solvents each having a predetermined boiling point and a polymer to the skin, by setting the Hansen solubility parameters of these two kinds of solvents to water to a prescribed range, respectively, allowing the compatibilities of the two kinds of solvents and the solubility of the polymer in each of the solvents to fall in a specified relation, respectively, primary particles are formed following drying of the liquid composition coated on the skin due to a temperature of the skin, and even when an inorganic pigment is not used, the high concealment is provided, the makeup deterioration is suppressed, and the makeup durability is improved.

Specifically, the present invention relates to a method for forming a coating film including a step of coating a liquid composition I containing a solvent A, a solvent B, and a polymer C to skin, wherein a boiling point of the solvent A is lower than 99° C., and a distance Ra of the Hansen solubility parameter of the solvent A to water as expressed by the following equation (1) is 36 or less, a boiling point of the solvent B is 150° C. or higher, and a distance Ra of the Hansen solubility parameter of the solvent B to water as expressed by the following equation (1) is 40 or more, and the solvent B is compatible with the solvent A, and the polymer C is soluble in the solvent A but insoluble in the solvent B, $$Ra=(4\times\Delta D^2+\Delta P^2+\Delta H^2)^{0.5} \quad (1)$$

wherein, $\Delta D$ is a difference of dispersing component in the Hansen solubility parameter between a solvent and water, $\Delta P$ is a difference of polar component in the Hansen solubility parameter between a solvent and water, and $\Delta H$ is a difference of a hydrogen-binding component in the Hansen solubility parameter between a solvent and water.

In accordance with the present invention, it is possible to provide a method for forming a coating film which is excellent in concealment of unevenness of the skin, hardly causes makeup deterioration, and is excellent in makeup durability.

[Forming Method of Coating Film]

The method for forming a coating film of the present invention is a method for forming a coating film including a step of coating a liquid composition I containing a solvent A, a solvent B, and a polymer C to skin (hereinafter also referred to as "step 1"), wherein a boiling point of the solvent A is lower than 99° C., and a distance Ra of the Hansen solubility parameter of the solvent A to water as expressed by the following equation (1) is 36 or less; a boiling point of the solvent B is 150° C. or higher, and a distance Ra of the Hansen solubility parameter of the solvent B to water as expressed by the following equation (1) is 40 or more; and the solvent B is compatible with the solvent A, and the polymer C is soluble in the solvent A but insoluble in the solvent B, $$Ra=(4\times\Delta D^2+\Delta P^2+\Delta H^2)^{0.5} \quad (1)$$

wherein, $\Delta D$ is a difference of dispersing component in the Hansen solubility parameter between a solvent and water, $\Delta P$ is a difference of polar component in the Hansen solubility parameter between a solvent and water, and $\Delta H$ is a difference of hydrogen-binding component in the Hansen solubility parameter between a solvent and water.

In the present invention, the wording "compatible" refers to a phenomenon in which in a mixed system containing the solvent A and the solvent B, the solvent A and the solvent B are mutually dissolved. The case where when the solvent A and the solvent B are mixed and allowed to stand, they are not separated in multiple phases, or the case where when the solvent A and the solvent B are mixed and subjected to a stirring operation, no phase separation is caused, so that they do not become cloudy, is judged such that the solvent A and the solvent B are in a compatibilized state with each other.

The polymer C is one which is soluble in the solvent A but insoluble in the solvent B and is dissolved in the liquid composition I.

In the present invention, the wording "the polymer C is soluble in the solvent A" means that the dissolved amount when the polymer C after drying at 105° C. for 2 hours and reaching a constant weight is dissolved in 100 g of the solvent A at 25° C. is 5 g or more. The aforementioned dissolve amount is preferably 10 g or more from the viewpoint of improving the whiteness and the concealment.

In the present invention, the wording "the polymer C is insoluble in the solvent B" means that the dissolved amount when the polymer C after drying at 105° C. for 2 hours and reaching a constant weight is dissolved in 100 g of the solvent B at 25° C. until it is saturated is less than 5 g. The foregoing dissolved amount is preferably 2 g or less from the viewpoint of improving the whiteness and the concealment.

The judgement regarding "compatible" or "soluble" is performed at 25° C.

In the present invention, the "Hansen solubility parameter" is expressed by dividing the solubility parameter (SP value) introduced by Hildebrand into three components (dispersing component D, polar component P, and hydrogen-binding component H). The D, P, and H of the respective solvents are described in detail in "HANSEN SOLUBILITY PARAMETERS" A User's Handbook Second Edition. In addition, the HSP values regarding a lot of solvents and resins are also described in Wesley L. Archer, "Industrial Solvents Handbook" and the like.

The D, P, and H of the respective solvents can also be determined using a software HSPiP of Charles Hansen Consulting, Inc. (Horsholm, Denmark, hansen-solubility-.com).

In the present invention, with respect to solvents registered in the database of HSPiP Version 4.1.03 (see the literatures of various HSP's), the values are adopted, and with respect to solvents not registered in the database, values estimated from the aforementioned HSPiP are adopted.

In accordance with the present invention, even when an inorganic pigment is not used, the concealment of unevenness of the skin (hereinafter also referred to simply as "concealment") is excellent, the makeup deterioration is hardly caused, and the makeup durability can be improved. Although the reason for this is not elucidated yet, the following may be considered.

In the method for forming a coating film of the present invention, the liquid composition I containing the solvent A and the solvent B which are different from each other with respect to the boiling point and the distance Ra of the Hansen solubility parameter to water and the polymer C which is soluble in the solvent A but insoluble in the solvent B is used. By coating such a liquid composition I on the skin, the solvent A having a low boiling point is volatilized due to a temperature of the skin, and the solubility parameters to water of the solvent A and solvent B fall within the specified ranges, respectively, and therefore, the solvent B compatibilized with the solvent A is phase-separated. Then, it may be considered that since the polymer C is soluble in the solvent A but insoluble in the solvent B, the polymer C coats the phase-separated solvent B, and coalescence of the solvent B is suppressed, whereby primary particles having a core-shell structure in which the solvent B constitutes the core, and the polymer C constitutes the shell are formed. As a result, it may be conjectured that the light is scattered due to the particle structure formed within the coating film, the high whiteness is expressed, and the concealment is improved.

In view of the fact that the primary particles of the obtained coating film are formed of the polymer C, since the refractive index of the coating film is close to the refractive index of a corneocyte of the skin as compared with an inorganic pigment, the sulcus cutis or pore part is coated with the coating film, so that the brightness between the sulcus cutis or pore part and the crista cutis part can be made close to each other without making the sulcus cutis or pore part noticeable unnaturally.

In addition, in the inside of the sulcus cutis, the primary particles having a core-shell structure are adsorbed to each other at a plurality of positions through the shell, and a polymer coating film with high elasticity is formed. Thus, even when deformations are brought on the sulcus cutis or wrinkles of the skin due to a change of facial expression or the like, the primary particles having been taken into the inside of the sulcus cutis or wrinkles are able to deform following the deformation and then reversibly return into an original state following the subsequent volume change. For this reason, the primary particles are not pushed out onto the skin surface, and the state of the coating film before deformation of the sulcus cutis or wrinkles can be kept. For this reason, it may be considered that the makeup deterioration is suppressed, even when the surface of the makeup coating film is scraped by clothes, fingers, or the like, cosmetic transfer is hardly caused, and the clothes, fingers, or the like can be prevented from being contaminated.

(Step 1: Coating Step)

The present invention includes coating a liquid composition I containing the solvent A, the solvent B, and the polymer C (hereinafter also referred to as "liquid composition I") to the skin.

<Liquid Composition I>

(Solvent A)

The liquid composition I according to the present invention contains the solvent A.

As for the solvent A, its boiling point is lower than 99° C., and the distance Ra of the Hansen solubility parameter of the solvent A to water as expressed by the aforementioned equation (1) is 36 or less. Furthermore, the solvent A is compatible with the solvent B and dissolves the polymer C therein. According to this, on the occasion of coating the liquid composition I on the skin, the solvent A having a low boiling point is volatilized, whereby phase separation between the solvent A and the solvent B can be caused.

The boiling point of the solvent A is lower than 99° C., preferably 98° C. or lower, more preferably 90° C. or lower, and still more preferably 80° C. or lower from the viewpoint of forming the primary particles and improving the concealment and the makeup durability, and is also preferably 50° C. or higher, more preferably 60° C. or higher, and still more preferably 70° C. or higher from the viewpoint of handling properties.

The distance Ra of the Hansen solubility parameter of the solvent A to water is 36 or less, preferably 32 or less, more preferably 30 or less, still more preferably 28 or less, and yet still more preferably 26 or less, and is also preferably 10 or more, more preferably 15 or more, still more preferably 20 or more, and yet still more preferably 22 or more, from the viewpoint of forming the primary particles and improving the concealment and the makeup durability.

The solvent A may be used alone or in combination of two or more thereof. In the case of using the solvent A in combination of two or more thereof, the boiling point of the solvent A and the distance Ra of the Hansen solubility parameter of the solvent A to water can be determined as a weighted average value resulting through weighing in terms of the content (% by mass) of each of the solvents.

The solvent A is preferably a monohydric alcohol having 1 or more and 4 or less carbon atoms from the viewpoint of improving the concealment and the makeup durability. Above all, more preferred is at least one selected from the group consisting of ethanol, propanol, isopropanol, and tert-butyl alcohol, still more preferred is ethanol.

(Solvent B)

The liquid composition I according to the present invention contains the solvent B.

As for the solvent B, its boiling point is 150° C. or higher, and the distance Ra of the Hansen solubility parameter of the solvent B to water as expressed by the aforementioned equation (1) is 40 or more. Furthermore, the solvent B is compatible with the solvent A and does not dissolve the polymer C therein. According to this, on the occasion of coating the liquid composition I on the skin, the solvent A having a low boiling point is volatilized, phase separation between the solvent A and the solvent B is caused, and the primary particles in which the solvent B is coated with the polymer C are formed.

The boiling point of the solvent B is 150° C. or higher, preferably 155° C. or higher, more preferably 160° C. or higher, still more preferably 165° C. or higher, and yet still more preferably 170° C. or higher from the viewpoint of forming the primary particles and improving the concealment and the makeup durability, and is also preferably 300° C. or lower, more preferably 270° C. or lower, still more preferably 250° C. or lower, yet still more preferably 230° C. or lower, even yet still more preferably 210° C. or lower, and even still more preferably 180° C. or lower from the viewpoint of handling properties.

The distance Ra of the Hansen solubility parameter of the solvent B to water is 40 or more, preferably 42 or more, and more preferably 44 or more, and is also preferably 60 or less, more preferably 57 or less, and still more preferably 55 or less, from the viewpoint of forming the primary particles and improving the concealment and the makeup durability.

The solvent B may be used alone or in combination of two or more thereof. In the case of using the solvent B in combination of two or more thereof, the boiling point of the solvent B and the distance Ra of the Hansen solubility parameter of the solvent B to water can be determined as a weighted average value resulting through weighing in terms of the content (% by mass) of each of the solvents.

From the viewpoint of improving the concealment and the makeup durability, the solvent B preferably contains at least one selected from the group consisting of a hydrocarbon oil and a silicone oil.

Examples of the hydrocarbon oil include α-olefin oligomers, liquid paraffins, liquid isoparaffins, such as isododecane, isohexadecane and hydrogenated polyisobutene, heavy liquid isoparaffins, liquid ozokerite, squalane, pristane, and squalene. The hydrocarbon oil is preferably a liquid isoparaffin, and more preferably at least one selected from the group consisting of isododecane and hydrogenated polyisobutene.

A weight average molecular weight of the hydrocarbon oil is preferably 150 or more, and more preferably 160 or more, and is also preferably 1,000 or less, more preferably 500 or less, and still more preferably 300 or less.

A viscosity at 20° C. of the hydrogenated polyisobutene is preferably 0.5 mPa·s or more, more preferably 0.7 mPa·s or more, and still more preferably 1 mPa·s or more, and is also preferably 30 mPa·s or less, more preferably 25 mPa·s or less, and still more preferably 20 mPa·s or less. The viscosity at 20° C. of the hydrogenated polyisobutene can be measured with an E-type viscometer by the method described in the section of Examples.

Examples of the silicone oil include linear silicone oils, such as trisiloxane; branched silicone oils, such as methyltrimethicone; and cyclic silicone oils, such as methylcyclopolysiloxane. Above all, preferred are trisiloxane and methyltrimethicone.

A weight average molecular weight of the silicone oil is preferably 150 or more, and more preferably 160 or more, and is also preferably 1,000 or less, more preferably 500 or less, and still more preferably 300 or less.

A viscosity at 25° C. of the silicone oil is preferably 0.5 mPa·s or more, and is also preferably 20 mPa·s or less, more preferably 10 mPa·s or less, still more preferably 5 mPa·s or less, and yet still more preferably 3 mPa·s or less. The viscosity at 25° C. of the silicone oil can be measured with an E-type viscometer by the method described in the section of Examples.

The solvent B may also be one containing, in addition to the hydrocarbon oil or the silicone oil, an additive, such as a moisturizer, an ultraviolet absorber, a pest repellent, a wrinkling-preventing agent, a fragrance, and a dye.

In the case where the solvent B contains at least one selected from the group consisting of a hydrocarbon oil and a silicone oil each having a weight average molecular weight of 150 or more and 1,000 or less, the content of at least one selected from the group consisting of a hydrocarbon oil and a silicone oil each having a weight average molecular weight of 150 or more and 1,000 or less in the solvent B is preferably 50% by mass or more, more preferably 70% by mass or more, and still more preferably 90% by mass or more from the viewpoint of improving the concealment and the makeup durability.

(Polymer C)

In the present invention, in a drying process of the liquid composition I coated on the skin, the polymer C coats the phase-separated solvent B and contributes to the formation of primary particles.

The polymer C is not particularly restricted so long as it is soluble in the solvent A but insoluble in the solvent B.

Examples of the polymer C include ionic polymers, such as an anionic polymer, a cationic polymer, and a betaine polymer; and nonionic polymers.

[Anionic Polymer]

The anionic polymer has an anionic group. Examples of the anionic group include groups that are capable of releasing a hydrogen ion upon dissociation thereof to exhibit acidity, such as a carboxy group (—COOM), a sulfonic acid group (—$SO_3$M), and a phosphoric acid group (—$OPO_3M_2$), or dissociated ion forms of these groups (such as —$COO^-$, —$SO_3^-$, —$OPO_3^{2-}$, and —$OPO_3^-$M). In the aforementioned chemical formulae, M represents a hydrogen atom, an alkali metal, ammonium, or an organic ammonium.

The anionic polymer is preferably an anionic polymer CI containing a constitutional unit derived from a monomer having an acidic group (hereinafter also referred to as "anionic polymer CI").

The monomer having an acidic group is preferably a monomer having a carboxy group, more preferably at least one selected from the group consisting of (meth)acrylic acid, crotonic acid, itaconic acid, maleic acid, fumaric acid, citraconic acid, and 2-methacryloyloxymethyl succinic acid, and still more preferably (meth)acrylic acid.

Here, the term "(meth)acrylic acid" means at least one selected from the group consisting of acrylic acid and methacrylic acid.

The anionic polymer CI is preferably a copolymer further containing a constitutional unit derived from other monomer than the monomer having an acidic group. Examples of the other monomer include hydrophobic monomers, such as a (meth)acrylate having a hydrocarbon group derived from an aliphatic alcohol and an aromatic group-containing monomer; and nonionic monomers.

Here, the term "(meth)acrylate" means at least one selected from the group consisting of acrylates and methacrylates.

The (meth)acrylate having a hydrocarbon group derived from an aliphatic alcohol is one having a hydrocarbon group derived from an aliphatic alcohol having preferably 1 or more and 22 or less carbon atoms, more preferably 1 or more and 12 or less carbon atoms, and still more preferably 1 or more and 8 or less carbon atoms. Examples of the (meth)acrylate include a (meth)acrylate having a linear alkyl group, a (meth)acrylate having a branched alkyl group, and a (meth)acrylate having an alicyclic alkyl group.

The aromatic group-containing monomer is preferably a vinyl monomer having an aromatic group having 6 or more and 22 or less carbon atoms, which may have a substituent containing a hetero atom, and more preferably at least one selected from the group consisting of a styrene-based monomer and an aromatic group-containing (meth)acrylate. A molecular weight of the aromatic group-containing monomer is preferably less than 500.

Examples of the styrene-based monomer include styrene, α-methylstyrene, 2-methylstyrene, vinyltoluene, and divinylbenzene.

Examples of the aromatic group-containing (meth)acrylate include phenyl (meth)acrylate, benzyl (meth)acrylate, and phenoxyethyl (meth)acrylate.

Examples of the nonionic monomer in the anionic polymer CI include (meth)acrylamide; N-vinyl-2-pyrrolidone; diacetone acrylamide; an N-alkyl (meth)acrylamide; a hydroxyalkyl (meth)acrylate; a polyalkylene glycol (meth)acrylate (n=2 to 30, n represents an average addition molar number of the oxyalkylene group; hereinafter the same); an alkoxypolyalkylene glycol (meth)acrylate (n=1 to 30); a phenoxy(ethylene glycol/propylene glycol copolymer) (n=1 to 30, in which n for ethylene glycol: n=1 to 29) (meth)acrylate.

Specific examples of commercially available nonionic monomers include NK ESTER M-20G, NK ESTER M-40G, NK ESTER M-90G, NK ESTER M-230G and the like, all of which are manufactured by Shin-Nakamura Chemical Co., Ltd.; and BLEMMER PE-90, BLEMMER PE-200, BLEMMER PE-350 and the like, BLEMMER PME-100, BLEMMER PME-200, BLEMMER PME-400 and the like, BLEMMER PP-500, BLEMMER PP-800, BLEMMER PP-1000 and the like, BLEMMER AP-150, BLEMMER AP-400, BLEMMER AP-550 and the like, BLEMMER 50PEP-300, BLEMMER 50POEP-800B, BLEMMER 43PAPE-600B and the like, all of which are manufactured by NOF Corporation.

Each of the aforementioned monomers can be used alone or in combination of two or more thereof.

A weight average molecular weight of the anionic polymer CI is preferably 5,000 or more, more preferably 10,000 or more, and still more preferably 20,000 or more, and is also preferably 1,000,000 or less, more preferably 500,000 or less, and still more preferably 200,000 or less. The weight average molecular weight of the anionic polymer CI is a molecular weight measured by the gel permeation chromatography (GPC) as expressed in terms of polystyrene.

Examples of commercially available products of the anionic polymer CI include acrylic acid/acrylic acid alkyl ester/(N-alkyl) acrylamide copolymers, such as ULTRAHOLD 8, ULTRAHOLD STRONG, and ULTRAHOLD POWER (all of which are manufactured by BASF Japan Ltd.), and AMPHOMER V-42 (manufactured by National Starch & Chemical Co.); carboxyvinyl polymers, such as CARBOPOL 980 and CARBOPOL 981 (all of which are manufactured by Lubrizol Advanced Materials, Inc.); (meth) acrylic acid/(meth)acrylic acid alkyl ester copolymers, such as DIAHOLD (manufactured by Mitsubishi Chemical Corporation); (acrylic acid/diacetone acrylamide) copolymer AMP or (acrylic acid/acrylic acid alkyl ester/diacetone acrylamide) copolymer AMP, such as PLASCIZE L-53P, PLASCIZE L-75CB, PLASCIZE L-9540B, PLASCIZE L-6466, and PLASCIZE L-3200B (all of which are manufactured by Goo Chemical Co., Ltd.); and (meth)acrylic acid/acrylic acid alkyl ester/polyvinylpyrrolidone copolymers, such as LUVIFLEX VBM35 (manufactured by BASF SE).

The anionic polymer CI is preferably a copolymer containing a constitutional unit derived from a monomer having an acidic group and a constitutional unit derived from a (meth)acrylic acid alkyl ester; more preferably a copolymer containing a constitutional unit derived from a monomer having an acidic group, a constitutional unit derived from a (meth)acrylic acid alkyl ester, and a constitutional unit derived from an (N-alkyl) (meth)acrylamide; still more preferably a (meth)acrylic acid/(meth)acrylic acid alkyl ester/(N-alkyl) (meth)acrylamide copolymer; and yet still more preferably an acrylic acid/acrylic acid alkyl ester/(N-alkyl) acrylamide copolymer.

[Cationic Polymer]

In the present invention, the wording "cationic" of the cationic polymer means that in the case where a non-neutralized polymer is dispersed or dissolved in pure water, the pH becomes larger than 7; in the case of a polymer having a quaternary ammonium group or the like, when it is dispersed or dissolved in pure water while making its counter ion as a hydroxide ion, the pH becomes larger than 7; or in the case where a polymer or the like is insoluble in pure water, and the pH cannot be distinctly measured, a zeta potential of the dispersion having the polymer or the like dispersed in pure water becomes positive.

The cationic polymer preferably has a basic group, such as a primary, secondary, or tertiary amino group, a quaternary ammonium group, and a hydrazino group, and more preferably has a quaternary ammonium group.

The basic group includes ones neutralized with an acid, such as hydrochloric acid, sulfuric acid, nitric acid, acetic acid, formic acid, maleic acid, fumaric acid, citric acid, tartaric acid, adipic acid, and lactic acid.

Examples of the cationic polymer include a natural cationic polymer and a synthetic cationic polymer.

The natural cationic polymer is a polymer obtained through an operation, such as extraction and purification, from a natural product or one resulting through chemical modification of the foregoing polymer, and examples thereof include ones having a glucose residue in the polymer skeleton. Specifically, examples thereof include cationized guar gum, cationized tara gum, cationized locust bean gum, cationized cellulose, a cationized hydroxyalkyl cellulose, and a cationic starch.

Examples of the synthetic cationic polymer include polyethyleneimine, polyallylamine or an acid-neutralized product thereof, a polyglycol-polyamine condensate, cationic polyvinyl alcohol, cationic polyvinylpyrrolidone, a cationic silicone polymer, a 2-(dimethylamino)ethyl methacrylate polymer or an acid-neutralized product thereof, poly(trimethyl-2-methacryloyloxyethylammonium chloride), an amine/epichlorohydrin copolymer, an N,N-dimethylaminoethyl methacrylic acid diethyl sulfate/vinylpyrrolidone copolymer, an N,N-dimethylaminoethyl methacrylic acid diethyl sulfate/N,N-dimethyl acrylamide/dimethacrylic acid polyethylene glycol copolymer, polydiallyldimethylammonium chloride, a diallyldimethylammonium chloride/acrylamide copolymer, a diallyldimethylammonium chloride/sulfur dioxide copolymer, a diallyldimethylammonium chloride/hydroxyethyl cellulose copolymer, a 1-allyl-3-methylimidazolium chloride/vinylpyrrolidone copolymer, an alkylamino (meth)acrylate/vinylpyrrolidone copolymer, an alkylamino (meth)acrylate/vinylpyrrolidone/vinyl caprolactam copolymer, a (3-(meth)acrylamidopropyl)trimethylammonium chloride/vinylpyrrolidone copolymer, and an alkylaminoalkyl acrylamide/alkyl acrylamide/(meth)acrylate/polyethylene glycol (meth)acrylate copolymer. These can be used alone or in combination of two or more thereof.

Above all, preferred are a cationic polymer CII-1 containing a constitutional unit derived from a monomer having a basic group (hereinafter also referred to as "cationic polymer CII-1") and a cationic silicone polymer CII-2.

[Cationic Polymer CII-1]

The cationic polymer CII-1 contains a constitutional unit derived from a monomer having a basic group. Examples of the foregoing basic group include the same groups as mentioned above.

Examples of the monomer having a basic group include amino group-containing monomers, such as an alkylamino (meth)acrylate, an N,N-dialkylaminoalkyl (meth)acrylate, N-[3-(dimethylamino)propyl](meth)acrylamide, and a diallyldialkylammonium, and acid-neutralized products or quaternized products thereof. These can be used alone or in combination of two or more thereof.

Examples of the acid for acid neutralization include hydrochloric acid, sulfuric acid, nitric acid, acetic acid, formic acid, maleic acid, fumaric acid, citric acid, tartaric acid, adipic acid, and lactic acid; and examples of the quaternizing agent include alkyl halides, such as methyl chloride, ethyl chloride, methyl bromide, and methyl iodide, and alkylating agents, such as dimethyl sulfate, diethyl sulfate, and di-n-propyl sulfate.

The cationic polymer CII-1 is preferably a homopolymer of a monomer having a basic group, a copolymer of a monomer having a basic group and other monomer than the foregoing monomer having a basic group, or a polycondensate; more preferably a copolymer of a monomer having a basic group and other monomer than the foregoing monomer having a basic group; still more preferably a copolymer containing a constitutional unit derived from a monomer having a basic group, a constitutional unit derived from the hydrophobic group as exemplified above for the anionic polymer CI, and a constitutional unit derived from the nonionic monomer as exemplified above for the anionic polymer CI; and yet still more preferably a copolymer containing a constitutional unit derived from an amino group-containing monomer, a constitutional unit derived from a (meth)acrylic acid alkyl ester, a constitutional unit derived from an N-alkyl (meth)acrylamide, and a constitutional unit derived from an alkoxy polyethylene glycol mono(meth)acrylate. The cationic polymer CII-1 is produced by copolymerizing raw material monomers containing these monomers by a known polymerization method, such as a block polymerization method, a solution polymerization method, a suspension polymerization method, and an emulsion polymerization method. Of these polymerization methods, a solution polymerization method is preferred.

From the viewpoint of improving the concealment and the makeup durability, at the time of producing the cationic polymer CII-1, the content of the monomer having a basic group, the hydrophobic monomer, and the nonionic monomer in the raw material monomers (the content as the non-neutralized content, hereafter the same), namely, the content of the constitutional unit derived from each of the components in the cationic polymer CII-1 is as follows.

The content of the monomer having a basic group is preferably 3% by mass, more preferably 5% by mass or more, and still more preferably 7% by mass or more, and is also preferably 35% by mass or less, more preferably 30% by mass or less, still more preferably 25% by mass or less, and yet still more preferably 20% by mass or less.

The content of the hydrophobic monomer is preferably 5% by mass or more, more preferably 10% by mass or more, and still more preferably 15% by mass or more, and is also preferably 35% by mass or less, more preferably 30% by mass or less, and still more preferably 25% by mass or less.

The content of the nonionic monomer is preferably 30% by mass or more, more preferably 40% by mass or more, and still more preferably 50% by mass or more, and is also preferably 85% by mass or less, more preferably 80% by mass or less, and still more preferably 75% by mass or less.

A weight average molecular weight of the cationic polymer CII-1 is preferably 5,000 or more, more preferably 7,000 or more, still more preferably 10,000 or more, yet still more preferably 50,000 or more, and even yet still more preferably 100,000 or more, and is also preferably 1,000,000 or less, more preferably 500,000 or less, still more preferably 300,000 or less, and yet still more preferably 200,000 or less, from the viewpoint of improving the concealment and the makeup durability.

The weight average molecular weight of the cationic polymer CII-1 can be measured by the method described in the section of Examples.

[Cationic Silicone Polymer CII-2]

The cationic silicone polymer CII-2 is preferably a poly (N-acylalkyleneimine)/organopolysiloxane copolymer containing an organopolysiloxane segment (x) (hereinafter also referred to simply as "segment (x)") and a poly(N-acylalkyleneimine) segment (y) composed of an alkylene group containing a cationic nitrogen atom binding to at least one silicon atom of the segment (x) and a repeating unit of an N-acylalkyleneimine represented by following general formula (1-1) (the poly(N-acylalkyleneimine) segment (y) will be hereinafter also referred to simply as "segment (y)").

(1-1)

In the formula, $R^1$ represents a hydrogen atom, an alkyl group having 1 or more and 22 or less carbon atoms, an aryl group having 6 or more and 22 or less carbon atoms, or an arylalkyl group or alkylaryl group having 7 or more and 22 or less carbon atoms; and a is 2 or 3.

The alkyl group represented by $R^1$ is preferably an alkyl group having 1 or more and 12 or less carbon atoms, and more preferably an alkyl group having 1 or more and 3 or less carbon atoms, such as a methyl group, an ethyl group, a n-propyl group, and an isopropyl group.

Examples of the aryl group represented by $R^1$ include a phenyl group and a naphthyl group.

Examples of the arylalkyl group represented by $R^1$ include a phenylalkyl group and a naphthylalkyl group, in which the carbon number of the alkyl group is 1 or more and 20 or less; and examples of the alkylaryl group include an alkylphenyl group and an alkylnaphthyl group, in which the carbon number of the alkyl group is 1 or more and 20 or less.

Although a degree of polymerization of the repeating unit represented by the general formula (1-1) in the segment (y), for example, it is preferably 1 or more and 500 or less, and more preferably 6 or more and 100 or less.

Examples of the organopolysiloxane that forms the segment (x) include compounds represented by the following general (1-2).

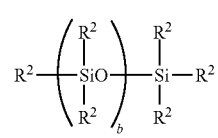

(1-2)

In the formula, $R^2$ represents an alkyl group having 1 or more and 22 or less carbon atoms, a phenyl group, or an alkyl group containing a nitrogen atom; though a plurality of the $R^2$ groups may be the same as or different from each other, at least one of them is an alkyl group containing a cationic nitrogen atom; and b is 100 or more and 5,000 or less.

In the general formula (1-2), among the alkyl groups having 1 or more and 22 or less carbon atoms as represented by $R^2$, an alkyl group having 1 or more and 12 or less carbon atoms is preferred, an alkyl group having 1 or more and 3 or less carbon atoms is more preferred, and a methyl group is still more preferred.

Examples of the alkyl group containing a nitrogen atom as represented by $R^2$ include alkyl groups having 2 or more and 20 or less carbon atoms which contains preferably 1 or more and 3 or less nitrogen atoms. The alkyl group containing a nitrogen atom may be existent in at least one silicon atom at an end or in a side chain of the organopolysiloxane, and the number of alkyl groups containing a nitrogen atom in the organopolysiloxane is preferably 1 or more and 300 or less, and more preferably 1 or more and 100 or less.

In the general formula (1-2), b is preferably 100 or more and 2,000 or less, and more preferably 350 or more and 1,500 or less.

A weight average molecular weight of the organopolysiloxane that forms the segment (x) is preferably 1,000 or more, more preferably 10,000 or more, and still more preferably 30,000 or more, and is also preferably 1,000,000 or less, more preferably 500,000 or less, and still more preferably 200,000 or less.

Examples of the alkylene group containing a nitrogen atom intervening in the bonding between the segment (x) and the segment (y) include alkylene groups having 2 or more and 20 or less carbon atoms which contains preferably 1 or more and 3 or less nitrogen atoms.

Specifically, examples of the nitrogen atom existing between carbon and carbon of the alkylene chain or at an end of the alkylene chain include (i) a secondary amine or a tertiary amine, (ii) an ammonium salt in which a hydrogen ion is added to a secondary amine or a tertiary amine, and (iii) a quaternary amine salt.

The poly(N-acylalkyleneimine)/organopolysiloxane copolymer is preferably one in which the segment (y) is bound to at least one silicon atom at an end or in a side chain of the segment (x) via the alkylene group containing a cationic nitrogen atom.

A mass ratio of the content of the segment (x) to the total content of the segment (x) and the segment (y) [{content of segment (x)}/{total content of segment (x) and segment (y)}] in the poly(N-acylalkyleneimine)/organopolysiloxane copolymer is preferably 0.1 or more, more preferably 0.3 or more, still more preferably 0.4 or more, and yet still more preferably 0.5 or more, and is also preferably 0.99 or less, more preferably 0.95 or less, and still more preferably 0.9 or less, from the viewpoint of improving the concealment and the makeup durability.

In this specification, the mass ratio [{content of segment (x)}/{total content of segment (x) and segment (y)}] is a ratio of a mass (Mx) of the segment (x) to the total amount of a mass (Mx) of the segment (x) and a mass (My) of the segment (y) in the poly(N-acylalkyleneimine)/organopolysiloxane copolymer.

The mass ratio [{content of segment (x)}/{total content of segment (x) and segment (y)}] can be determined by dissolving 5% by mass of the poly(N-acylalkyleneimine)/organopolysiloxane copolymer in deuterated chloroform and calculating an integration ratio of an alkyl group or a phenyl group in the segment (x) and a methylene group in the segment (y) through a nuclear magnetic resonance ($^1$H-NMR) analysis.

A weight average molecular weight of the poly(N-acylalkyleneimine)/organopolysiloxane copolymer is preferably 10,000 or more, more preferably 50,000 or more, and still more preferably 70,000 or more, and is also preferably 1,000,000 or less, more preferably 500,000 or less, and still more preferably 200,000 or less, from the viewpoint of improving the concealment and the makeup durability. The weight average molecular weight of the poly(N-acylalkyleneimine)/organopolysiloxane copolymer can be calculated from the weight average molecular weight of the organopolysiloxane that forms the segment (x) and the aforementioned mass ratio [{content of segment (x)}/{total content of segment (x) and segment (y)}].

Suitable examples of the poly(N-acylalkyleneimine)/organopolysiloxane copolymer include a poly(N-formylethyleneimine)/organopolysiloxane copolymer, a poly(N-acetylethyleneimine)/organopolysiloxane copolymer, and a poly(N-propionylethyleneimine)/organopolysiloxane copolymer.

The poly(N-acylalkyleneimine)/organopolysiloxane copolymer can be, for example, obtained by a method of allowing the (N-acylalkyleneimine) that is a ring-opening polymer of a cyclic imino ether and the organopolysiloxane that forms the segment (x) to react with each other. More specifically, the poly(N-acylalkyleneimine)/organopolysiloxane copolymer can be, for example, obtained by the method described in JP 2011-126978 A. The poly(N-acylalkyleneimine)/organopolysiloxane copolymer to be used as the cationic silicone polymer CII-2 can be used alone or in combination of two or more thereof.

[Betaine Polymer]

In the present invention, examples of the betaine polymer include a copolymer of a monomer having an anionic group and a monomer having a cationic group, a polymer or copolymer of a betaine monomer, a polymer having an anionic group introduced into a cationic polymer, and a polymer having the aforementioned basic group introduced into an anionic polymer. Above all, preferred is a polymer containing a betaine structure in a side chain thereof, and more preferred is a betaine polymer CIII containing a constitutional unit derived from a betaine monomer.

The betaine monomer is preferably a monomer containing a betaine structure and a (meth)acrylamide structure, more preferably at least one selected from the group consisting of a carboxybetaine monomer, a sulfobetaine monomer, and a phosphobetaine monomer, and still more preferably a carboxybetaine monomer.

Examples of the betaine polymer include polymethacryloylethyl dimethylbetaine, an N-methacryloyloxyethyl-N,N-dimethylammonium-α-N-methylcarboxybetaine/methacrylic acid alkyl ester copolymer, a methacryloylethyldimethylbetaine/methacryloylethyltrimethylammonium chloride/2-hydroxyethyl methacrylate copolymer, a methacryloylethyldimethylbetaine/methacryloyethyltrimethylammonium chloride/methacrylic acid/methoxypolyethylene glycol copolymer, and an octylacrylamide/acrylate/butylaminoethyl methacrylate copolymer. Above all, an N-methacryloyloxyethyl-N,N-dimethylammonium-α-N-methylcarboxybetaine/methacrylic acid alkyl ester copolymer is preferred.

A weight average molecular weight of the betaine polymer is preferably 5,000 or more, and more preferably 10,000 or more, and is also preferably 1,000,000 or less, more preferably 500,000 or less, and still more preferably 300,000 or less, from the viewpoint of improving the concealment and the makeup durability. The weight average molecular weight of the betaine polymer is a molecular weight measured by the gel permeation chromatography (GPC) as expressed in terms of polystyrene.

Examples of commercially available betaine polymers include PLASCIZE L-410W, PLASCIZE L-402W, PLASCIZE L-440, PLASCIZE L-440W, PLASCIZE K-450, and PLASCIZE L-450W (all of which are a trade name, manufactured by Goo Chemical Co., Ltd.); YUKA FORMER SM and YUKA FORMER 301 (all of which are a trade name, manufactured by Mitsubishi Chemical Corporation); RAM RESIN-1000, RAM RESIN-2000, RAM RESIN-3000, and RAM RESIN-4000 (all of which are a trade name, manufactured by Osaka Organic Chemical Industry Ltd.); MERQUAT PLUS 3330 (a trade name, manufactured by Lubrizol Japan Ltd.); and UNFOAMER 28-4910 and UNFOAMER LV-71 (all of which are a trade name, manufactured by Akzo Nobel N.V.).

[Nonionic Polymer]

Examples of the nonionic polymer include polymers having a constitutional unit derived from a nonionic monomer; and water-soluble polysaccharides (such as a cellulose-based polymer, a gum-based polymer, and a starch-based polymer) and derivatives thereof.

Examples of the nonionic monomer in the nonionic polymer include (meth)acrylates having a hydrocarbon group derived from an aliphatic alcohol having 1 or more and 22 or less carbon atoms; N-vinyl-2-pyrrolidone; vinyl alcohol; polyalkylene glycol (meth)acrylates (n=1 to 30); alkoxypolyalkylene glycol mono(meth)acrylates (n=1 to 30); and (meth)acrylamides and derivatives thereof.

The nonionic polymer may further contain a constitutional unit derived from other monomer than the nonionic monomer. Examples of the other monomer include the aforementioned styrene-based monomers; the aforementioned aromatic group-containing (meth)acrylates; and vinyl acetate.

Specifically, examples of the nonionic polymer include polyvinyl alcohol, polyvinyl acetal, polyurethanepolyurea, polyvinylpyrrolidone, copolymers of vinylpyrrolidone and other nonionic monomer, such as a vinylpyrrolidone/vinyl acetate copolymer, cellulose-based polymers, such as a hydroxyalkyl cellulose, polyethylene glycol, polypropylene glycol, polyglycerin, polyvinyl alcohol, pullulan, guar gum, poly(N,N-dimethylacrylamide), poly(N-vinylacetamide), poly(N-vinylformamide), and a poly(2-alkyl-2-oxazoline). Above all, polyvinyl acetal and polyurethanepolyurea are preferred.

Examples of commercially available nonionic polymers include polyvinyl butyral, such as S-LEC B Series (which are a trade name, manufactured by Sekisui Chemical Co., Ltd.); polyurethanepolyurea, such as BAYCUSAN Series (which are a trade name, manufactured by Covestro Japan Ltd.); hydroxyethyl cellulose, such as HEC DAICEL SE900, HEC DAICEL SE850, HEC DAICEL SE600, HEC DAICEL SE550, and HEC DAICEL SE400 (all of which are a trade name, manufactured by Daicel FineChem Ltd.); highly polymerized polyethylene glycol, such as POLYOX WSR N-12, POLYOX WSR N-60K, and POLYOX WSR 301 (all of which are a trade name, manufactured by The Dow Chemical Company); PEO-27, PEO-18, PEO-15, and PEO-8 (all of which are a trade name of polyethylene oxide, manufactured by Sumitomo Seika Chemicals Co., Ltd.); polyvinylpyrrolidone, such as LUVISKOL K90, LUVISKOL K80, and LUVISKOL K30 (all of which are a trade name, manufactured by BSAF SE); and polyvinyl alcohol, such as GOHSENOL Series (which are a trade name, manufactured by The Nippon Synthetic Chemical Industry Co., Ltd.).

In the present invention, from the viewpoint of improving the concealment and the makeup durability, the dissolved amount of the polymer C in water is preferably less than 5 g in terms of the dissolved amount when the polymer C after drying at 105° C. for 2 hours and reaching a constant weight is dissolved in 100 g of water at 25° C. until it is saturated.

In the case where the polymer C is an anionic polymer, the aforementioned dissolved amount is the dissolved amount when the anionic group of the polymer C is neutralized with sodium hydroxide to an extent of 100%. In the case where the polymer C is a cationic polymer, the aforementioned dissolved amount is the dissolved amount when the cationic group of the polymer C is neutralized with hydrochloric acid to an extent of 100%.

In the present invention, from the viewpoint of improving the concealment and the makeup durability, the polymer C is preferably an amphipathic polymer which is insoluble in the solvent B but has affinity to the solvent B and which also has affinity to water; and more preferably an ionic polymer. It is still more preferred that the polymer C contains a polymer containing, as the monomer constitutional unit, at least one selected from the group consisting of a monomer having an acidic group, a monomer having a basic group, and a betaine monomer; and it is yet still more preferred that the polymer C contains at least one selected from the group consisting of the anionic polymer CI, the cationic polymer CII-1, the cationic silicone polymer CII-2, and the betaine polymer CIII.

Above all, the polymer C is preferably a combination of two or more polymers; more preferably one containing the anionic polymer CI and at least one selected from the group consisting from the cationic polymer CII-1, the cationic silicone polymer CII-2, and the betaine polymer CIII; still more preferably one containing the anionic polymer CI and at least one selected from the group consisting of the cationic polymer CII-1 and the betaine polymer CIII; and yet still more preferably one containing the anionic polymer CI and the betaine polymer CIII.

A viscosity at 20° C. of the liquid composition I is preferably 1 mPa·s or more, more preferably 5 mPa·s or more, and still more preferably 10 mPa·s or more, and is also preferably 1,000 mPa·s or less, more preferably 700 mPa·s or less, still more preferably 300 mPa·s or less, yet still more preferably 200 mPa·s or less, even yet still more preferably 100 mPa·s or less, and even still more preferably 50 mPa·s or less. By regulating the viscosity of the liquid composition I, the formed primary particles are accumulated in the sulcus cutis, whereby the concealment can be improved. The viscosity at 20° C. of the liquid composition I is measured by the method described in the section of Examples.

The liquid composition I according to the present invention may further contain, as an arbitrary component, a component which is used for a cosmetic composition, such as a dye, an organic pigment, an inorganic pigment, an ultraviolet scattering agent, an ultraviolet absorber, a fragrance, a beauty ingredient, a medicinal ingredient, a pH control agent, a moisturizer, an antioxidant, a disinfectant, and an antiseptic agent. Each of them may be used alone or in combination of two or more.

(Production of Liquid Composition I)

The liquid composition I can be obtained by mixing the solvent A, the solvent B, and the polymer C, and optionally, the aforementioned arbitrary component, followed by stirring. Although the mixing order is not particularly restricted, it is preferable to include a step of first mixing the solvent A and the polymer C to dissolve the polymer C in the solvent A, thereby obtaining a solution of the polymer C, and then adding the solvent B to the foregoing solution. If desired, the aforementioned arbitrary component may be further added and mixed.

From the viewpoint of improving the concealment and the makeup durability, the content of each of the components in the liquid composition I is as follows.

The content of the solvent A in the liquid composition I is preferably 50% by mass or more, more preferably 60% by mass or more, and still more preferably 65% by mass or more, and is also preferably 90% by mass or less, more preferably 80% by mass or less, and still more preferably 75% by mass or less.

The content of the solvent B in the liquid composition I is preferably 5% by mass or more, more preferably 7% by mass or more, and still more preferably 10% by mass or more, and is also preferably 40% by mass or less, more preferably 30% by mass or less, and still more preferably 25% by mass or less.

A mass ratio of the content of the solvent A to the solvent B in the liquid composition I [(solvent A)/(solvent B)] is preferably 0.01 or more, more preferably 0.1 or more, still more preferably 0.5 or more, yet still more preferably 1 or more, and even yet still more preferably 1.5 or more, and is also preferably 50 or less, more preferably 30 or less, still more preferably 10 or less, and yet still more preferably 7 or less.

The content of the polymer C in the liquid composition I is preferably 2% or more, more preferably 5% by mass or more, and still more preferably 7% by mass or more, and is also preferably 20% by mass or less, more preferably 17% by mass or less, and still more preferably 15% by mass or less.

In the case where the polymer C contains the anionic polymer CI and at least one selected from the group consisting of the cationic polymer CII-1 and the betaine polymer CIII, the total content of the anionic polymer CI and at least one selected from the group consisting of the cationic polymer CII-1 and the betaine polymer CIII in the polymer C, or the total content of the anionic polymer CI, the cationic polymer CII-1, the cationic silicone polymer CII-2, and the betaine polymer CIII in the polymer C is preferably 60% by mass or more, more preferably 70% by mass or more, still more preferably 80% by mass or more, and yet still more preferably 90% by mass or more, and is also preferably 100% by mass or less, and yet still more preferably 100% by mass.

In the case where the polymer C contains the anionic polymer CI and the betaine polymer CIII, a mass ratio of content between the anionic polymer CI and the betaine polymer CIII [(content of anionic polymer CI)/(content of betaine polymer CIII)] is preferably 0.1 or more, more preferably 0.3 or more, still more preferably 0.5 or more, and yet still more preferably 0.7 or more, and is also preferably 9 or less, more preferably 5 or less, still more preferably 3 or less, and yet still more preferably 2 or less.

A mass ratio of the content of the polymer C to the total content of the solvent A and the solvent B in the liquid composition I [(polymer C)/{(solvent A)+(solvent B)}] is preferably 0.01 or more, more preferably 0.05 or more, still more preferably 0.07 or more, and yet still more preferably 0.1 or more, and is also preferably 1 or less, more preferably 0.5 or less, still more preferably 0.3 or less, and yet still more preferably 0.2 or less.

The content of the inorganic pigment in the liquid composition I is preferably 10% by mass or less, more preferably 5% by mass or less, still more preferably 3% by mass or less, yet still more preferably 1% by mass or less, and even yet still more preferably 0% by mass.

[Coating]

In the present invention, coating of the liquid composition I can be performed by a coating method which is typically adopted on the occasion of applying to the skin under temperature and humidity conditions for daily living. Then, by drying the coating film composed of the liquid composition I coated on the skin, the coating film is formed.

The coating amount of the liquid composition I on the skin is preferably 1 mg/cm$^2$ or more, more preferably 2 mg/cm$^2$ or more, and still more preferably 3 mg/cm$^2$ or more, and is also preferably 10 mg/cm$^2$ or less, more preferably 7 mg/cm$^2$ or less, and still more preferably 5 mg/cm$^2$ or less.

A thickness T of the coating film before drying (hereinafter also referred to as "wet film thickness") is preferably 10 μm or more, more preferably 20 μm or more, and still more preferably 30 μm or more, and is also preferably 300 μm or less, more preferably 200 μm or less, and still more preferably 150 μm or less.

In the present invention, though drying of the coating film can be thoroughly performed by means of natural drying at a skin temperature, it may be performed by means of blast drying, warm air drying, or the like from the viewpoint of quickly the drying.

In the case of performing warm air drying, though the temperature at the time of drying of the coating film is not particularly restricted, it is preferably 40° C. or higher, more preferably 50° C. or higher, and still more preferably 55° C. or higher, and is also preferably 80° C. or lower, more preferably 70° C. or lower, and still more preferably 65° C. or lower.

A drying time of the coating film is preferably 5 minutes or more, more preferably 7 minutes or more, and still more preferably 10 minutes or more, and is also preferably 30 minutes or less, and more preferably 20 minutes or less.

From the viewpoint of improving the concealment and the makeup durability, the primary particles according to the present invention are preferably a primary particle having a core-shell structure in which the solvent B constitutes the core, and the polymer C constitutes the shell, and more preferably a hollow primary particle formed by evaporating the solvent B included in the core part of the primary particle. On the occasion of forming the hollow primary particle, fine pores (openings) are occasionally formed in the shell part. In this case, even when deformations are brought on the sulcus cutis or wrinkles of the skin due to a change of facial expression or the like, the hollow primary particles having been taken into the inside of the sulcus cutis or wrinkles are able to reversibly return into an original state following the volume change of the sulcus cutis or wrinkles owing to deformation of the particles or pushing out of the air. For this reason, it may be considered that pushing out of the hollow primary particles onto the skin surface is further suppressed, the state of the coating film before deformation of the sulcus cutis or wrinkles can be kept well, and the makeup durability can be improved.

The hollow primary particles can be formed by controlling the kind of the solvent B or the drying condition of the coating film after coating on the skin to evaporate the solvent B included in the core part.

(Step 2: Droplet Applying Step)

From the viewpoint of improving the concealment and the makeup durability, the forming method of the present invention preferably includes a step of after the step 1 of coating the liquid composition I on the skin and before drying the coating film composed of the liquid composition I, further applying droplets of the liquid II containing water to the liquid composition I on the skin (the foregoing step will be also referred to as "step 2"). According to this, the phase separation between the solvent A and the solvent B quickly proceeds, and the formation of the primary particles in which the solvent B is coated with the polymer C is accelerated.

<Liquid II>

The liquid II according to the present invention contains water, but it may also contain other liquid than water.

As for the other liquid, a monohydric alcohol having 1 or more and 4 or less carbon atoms is preferred, and example thereof include ethanol, propanol, isopropanol, and tert-butyl alcohol. Above all, from the viewpoint of improving the concealment and the makeup durability, preferred is at least one selected from the group consisting of ethanol, propanol, isopropanol, and tert-butyl alcohol, more preferred is ethanol.

A content of water in the liquid II is preferably 50% by mass or more, more preferably 70% by mass or more, and still more preferably 90% by mass or more, and is also preferably 100% by mass or less, and yet still more preferably 100% by mass.

An applied amount of the droplets is preferably 0.01 mg/cm$^2$ or more, more preferably 0.05 mg/cm$^2$ or more, and still more preferably 0.1 mg/cm$^2$ or more, and is also preferably 10 mg/cm$^2$ or less, more preferably 7 mg/cm$^2$ or less, and still more preferably 5 mg/cm$^2$ or less.

An average diameter of the droplets is preferably 0.01 μm or more, more preferably 0.1 μm or more, and still more preferably 1 μm or more, and is also preferably 50 μm or less, more preferably 30 μm or less, and still more preferably 10 μm or less, from the viewpoint of improving the concealment and the makeup durability.

As a method for applying droplets, from the viewpoint of improving the concealment and the makeup durability, it is preferred to atomize the droplets on the coating film composed of the liquid composition I on the skin by using an apparatus of generating fine droplets. The apparatus of generating fine droplets is not particularly limited, and for example, it is preferred to use an atomizer, such as a jet type atomizer, an ultrasonic atomizer, and a mesh type atomizer.

An atomizing capacity of the atomizer is preferably 0.01 mL/min or more, more preferably 0.1 mL/min or more, and still more preferably 0.3 mL/min or more, and is also preferably 10 mL/min or less, more preferably 7 mL/min or less, and still more preferably 5 mL/min or less.

An atomizing time of the atomizer is preferably 1 second or more, and more preferably 3 seconds or more, and is also preferably 30 seconds or less, more preferably 20 seconds or less, and still more preferably 10 seconds or less.

As for the application of the droplets, the droplets may be applied to the whole of an area to which the liquid composition I has been coated on the skin, or may be applied to a part of the foregoing area.

The application of the droplets can be performed under temperature and humidity conditions for daily living.

An interval of time between the coating step and the droplet applying step is not particularly restricted so long as the droplet applying step is quickly performed before the liquid composition I on the skin is dried.

An average particle diameter of the primary particles contained in the coating film which is formed by the present invention is preferably 0.1 µm or more, and more preferably 1 µm or more from the viewpoint of improving the strength of the coating film and improving the makeup durability, and is also preferably 5 µm or less, and more preferably 3 µm or less from the viewpoint of improving the concealment.

The average particle diameter of the primary particles can be measured by observing the formed coating film with a scanning electron microscope and subjecting the obtained scanning electron microscopic photograph to image processing using an image analysis software "ImageJ" (manufactured by National Institutes of Health). Specifically, the average particle diameter of the primary particles can be measured by the method described in the section of Examples.

It is preferred that the coating film which is formed by the present invention contains secondary particles having primary particles accumulated therein. In the present invention, it may be considered that following the volatilization of the solvent A and the surface alignment of the formed primary particles, a cell-shaped convection structure regularly divided within the coating film, so-called "Benard cells", is generated, whereby the primary particles are accumulated due to the Benard convection in each cell to form secondary particles. The coating film containing such secondary particles has a structure close to the surface relief structure of an actual skin, and therefore, a coating film giving a natural impression can be formed.

According to the method for forming a coating film of the present invention, since the coating film which is excellent in concealment, hardly causes makeup deterioration, and is excellent in makeup durability can be obtained even without using an inorganic pigment, it can be applied as a forming method of a makeup coating film using a makeup base, a foundation, a concealer; an ultraviolet-light shielding cosmetic, such as a sunscreen milk lotion and a sunscreen cream; a makeup cosmetic, such as a cheek rouge, an eye shadow, a mascara, an eyeliner, an eyebrow, an overcoat agent, and a lipstick, or the like; or a forming method of a coating film for unevenness correction or protection of the skin; or the like. Above all, the foregoing forming method is preferably adopted for a forming method of a coating film for a cosmetic base or a coating film for unevenness correction or protection of the skin. The liquid composition I can take any preparation form such as a cream form, a gel form, a milk lotion form, a solution form, and a spray form.

In the case of adopting the foregoing method for the forming method of a coating film for makeup base, the unevenness of the skin of sulcus cutis or pores of the skin can be concealed by using the liquid composition I as the composition for makeup base and coating the liquid composition I to the skin to form a coating film on the skin surface by the forming method of the present invention, and then coating a foundation on the coating film.

In the case of adopting the foregoing method for the forming method of a coating film for unevenness correction or protection of the skin, the unevenness of the skin can be concealed, or the skin can be protected by using the liquid composition I as the composition for unevenness correction or protection of the skin and coating the liquid composition I on remarkable unevenness on the skin, such as severe acne scar, scar, and burn scar, or on the skin requiring protection from chemical or physical irritations to form a coating film on the skin surface by the forming method of the present invention. Similar to the aforementioned makeup base, it is also possible to coat a foundation on the coating film.

EXAMPLES

In the following Synthesis Examples, Preparation Examples, Examples, and Comparative Examples, the terms "parts" and "%" are "parts by mass" and "% by mass", respectively unless otherwise indicated. The measurements of physical properties of polymers and so on were performed by the following methods.

(1) Measurement of Weight Average Molecular Weight of Cationic Polymer CII-1

The measurement was performed using, as an eluent, a liquid in which phosphoric acid and lithium bromide were dissolved in concentrations of 60 mmol/L and 50 mmol/L, respectively in N,N-dimethylformamide by means of the gel permeation chromatography [GPC apparatus (HLC-8320GPC), manufactured by Tosoh Corporation, columns (TSKgel Super AWM-H, TSKgel Super AW3000, TSKgel guardcolumn Super AW-H), manufactured by Tosoh Corporation, flow rate: 1 mL/min] while using, as a standard substance, mono-dispersed polystyrene kits having already-known molecular weights [PStQuickB (F-550, F-80, F-10, F-1, A-1000) and PStQuick C (F-288, F-40, F-4, A-5000, A-500), all of which are manufactured by Tosoh Corporation].

As a measurement sample, one prepared by mixing 0.1 g of the cationic polymer CII-1 and 10 mL of the aforementioned eluent in a glass vial, stirring the mixture with a magnetic stirrer at 25° C. for 10 hours, and filtering the resultant with a syringe filter (DISMIC-13HP PTFE, 0.2 µm, manufactured by Advantech Co., Ltd.) was used.

(2) Measurement of Number Average Molecular Weight of Poly(N-propionylethyleneimine)

The measurement was performed using, as an eluent, 1 mmol/L of FARMIN DM20 (a trade name, manufactured by Kao Corporation)/chloroform by means of the gel permeation chromatography [measurement columns: two columns (K-804L), manufactured by Showa Denko K.K., connected in series, flow rate: 1 mL/min, column temperature: 40° C., detector: differential refractometer] while using, as a standard substance, polystyrene having an already-known molecular weight. 100 μL of the measurement sample having a concentration of 5 mg/mL was used.

(3) Measurement of Viscosity

The viscosity was measured with an E-type viscometer RE80, manufactured by Toki Sangyo Co., Ltd. at a rotation number of 100 rpm for a measurement time of 1 minute by using a standard rotor (1° 34'×R24).

The measurement of the viscosity was performed at 20° C. for hydrogenated polyisobutene, 25° C. for the silicone oil, and 20° C. for the liquid composition I, respectively.

(4) Measurement of Wet Film Thickness T by Wire Bar-Coating

In an environmental chamber, the temperature and humidity of which were controlled at a temperature of 25° C. and a humidity of 50%, an A4-sized transparent PET film (a trade name: LUMIRROR T-60, manufactured by Toray Industries, Inc., film thickness: 75 μm), the weight of which had been measured in advance, was placed on a desktop coater (a trade name: TC-1, manufactured by Mitsui Electric Co., Ltd.), and then, a wire bar to be wanted to confirm the wet film thickness was set. Subsequently, about 2 to 6 mL of a mixed solution of 10% of ethanol, 50% of water, and 40% of glycerin was dropped using a dropper, and immediately thereafter, the mixed solution was coated on the PET film using the above-set wire bar at a traveling speed of the wire bar of 1 m/min. On the occasion of coating, it was confirmed that the aforementioned mixed solution uniformly spread on the entire surface of the PET film, and the liquid leaked from the end. Subsequently, the weight of the coated PET film was immediately measured and corrected with a specific gravity of the aforementioned mixed solution, thereby calculating the wet film thickness T on the occasion of using the wire bar.

(5) Measurement of Average Particle Diameter of Primary Particles

An observation image of a polymer coating film surface was taken with an optical microscope (manufactured by Hirox Co., Ltd., a trade name: RH-2000) at a magnification of 2,500 times and subjected to image processing using image analysis software (manufactured by National Institutes of Health, "ImageJ") to measure the average particle diameter of the primary particles contained in the coating film.

On the occasion of photographing with the optical microscope, the observation image was saved by adjusting the luminance and the contrast such that a proportion of pixels reaching a maximum luminance value was 1% or less, and an average value of the luminance value fell within a range of 40% to 60% of the maximum luminance value. The observation image was converted to an 8-bit greyscale image by using an image conversion function of the ImageJ.

Subsequently, the scale setting was performed in conformity with the magnification of the optical microscope. According to this scale setting, data of the particle diameter calculated by the subsequent operation is converted into an actual size. As an example, in the case of the magnification of 2,500 times, the conversion was performed such that the length of 1 mm is composed of 15,840 pixels.

The subtract background processing was performed. On this occasion, the rolling ball radius is set to the same size as that of the generally observed primary particles. Specifically, the primary particles having a diameter of about 3 μm occupy the majority, and in the case where the length of 1 mm is composed of 15,840 pixels, the rolling ball radius is set to 50 pixels. According to this, the noise component on the photographing, which is smaller than the primary particle diameter, can be cut out.

Subsequently, the area of the primary particles was subjected to binary coded processing by using a threshold function as the image adjustment function of the ImageJ.

In this specification, the "binary coded processing" means a processing in which the case where the luminance value of the image is the designated value (threshold value) or more is defined as white, whereas the case where it is less than the designated value is defined as black. In the image obtained through the observation, the shell of the primary particles is expressed to be a high luminance because of a high existent density of polymer, and the core portion is expressed to be a low luminance. According to this, it becomes possible to obtain a distinct image in which a shadow is sufficient for measuring the average particle diameter of the primary particles.

The obtained binary image was subjected to "Analyze Particles" of the ImageJ.

Particles in which the image end is cut off, particles having a major axis of 1/10 of the generally observed primary particle diameter (particles with less than 5 pixels in the aforementioned setting), and particles of a roundness of less than 0.5 were excluded from the measurement object, and an average value of the major axis of at least 300 particles was defined as the average particle diameter of the primary particles.

Details of the respective components are as follows.

(Anionic Polymer CI)

ULTRAHOLD 8: An acrylic acid/acrylic acid alkyl ester/(N-alkyl) acrylamide copolymer (manufactured by BASF Japan Ltd., a trade name: ULTRAHOLD 8), powder with a solid component content of 100%

ULTRAHOLD STRONG: An acrylic acid/acrylic acid alkyl ester/(N-alkyl) acrylamide copolymer (manufactured by BASF Japan Ltd., a trade name: ULTRAHOLD STRONG), powder with a solid component content of 100%

ULTRAHOLD POWER-dry: A powder prepared by drying a solution of an acrylic acid/acrylic acid alkyl ester/(N-alkyl) acrylamide copolymer (solid component content: 32%) (manufactured by BASF Japan Ltd., a trade name: ULTRAHOLD POWER)

(Cationic Polymer CII-1)

Cationic polymer 1: A copolymer obtained in the following Synthesis Example 1

Cationic polymer 2: A copolymer obtained in the following Synthesis Example 2

(Cationic Silicone Polymer CII-2)

Cationic silicone polymer 1: A poly(N-propionylethyleneimine)/dimethylpolysiloxane copolymer obtained in the following Synthesis Example 3

Cationic silicone polymer 2: A poly(N-propionylethyleneimine)/dimethylpolysiloxane copolymer obtained in the following Synthesis Example 4

Cationic silicone polymer 3: A poly(N-propionylethyleneimine)/dimethylpolysiloxane copolymer obtained in the following Synthesis Example 5

(Betaine Polymer CIII)

YUKA FORMER SM-dry: A powder prepared by drying an ethanol solution of an N-methacryloyloxyethyl-N,N-dimethylammonium-α-N-methylcarboxybetaine/methacrylic acid alkyl ester copolymer (solid component content: 30%) (manufactured by Mitsubishi Chemical Corporation, a trade name: YUKA FORMER SM-dry)

RAM RESIN 1000-dry: A powder prepared by drying an ethanol solution of an N-methacryloyloxyethyl-N,N-dimethylammonium-α-N-methylcarboxybetaine/methacrylic acid alkyl ester copolymer (solid component content: 30%) (manufactured by Osaka Organic Chemical Industry Ltd., a trade name: RAM RESIN-1000, molecular weight: 100,000)

RAM RESIN 2000-dry: A powder prepared by drying an ethanol solution of an N-methacryloyloxyethyl-N,N-dimethylammonium-α-N-methylcarboxybetaine/methacrylic acid alkyl ester copolymer (solid component content: 30%) (manufactured by Osaka Organic Chemical Industry Ltd., a trade name: RAM RESIN-2000, molecular weight: 40,000)

RAM RESIN 3000-dry: A powder prepared by drying an ethanol solution of an N-methacryloyloxyethyl-N,N-dimethylammonium-α-N-methylcarboxybetaine/methacrylic acid alkyl ester copolymer (solid component content: 30%) (manufactured by Osaka Organic Chemical Industry Ltd., a trade name: RAM RESIN-3000, molecular weight: 40,000)

(Nonionic Polymer)

Polyvinyl butyral: S-LEC BM-1 (manufactured by Sekisui Chemical Co., Ltd., a trade name), powder with a solid component content of 100% Polyurethanepolyurea: A powder prepared by drying BAYCUSAN C2000 (manufactured by Covestro Japan Ltd., a trade name, an ethanol solution of polyurethane-64 with a solid component content of 40%)

(Solvent B)

[Hydrocarbon Oil]

PARLEAM 3: Hydrogenated polyisobutene (manufactured by NOF Corporation, a trade name: PARLEAM 3, boiling point: 179° C., Ra: 45, viscosity: 1.4 mPa·s)

PARLEAM 4: Hydrogenated polyisobutene (manufactured by NOF Corporation, a trade name: PARLEAM 4, boiling point: 262° C., Ra: 45, viscosity: 3.7 mPa·s)

[Silicone Oil]

KF-96A-1cs: Trisiloxane (manufactured by Shin-Etsu Chemical Co., Ltd., a trade name: KF-96A-1cs, Ra: 45, boiling point: 153° C., viscosity: 0.9 mPa·s)

TMF-1.5: Methyltrimethicone (manufactured by Shin-Etsu Chemical Co., Ltd., a trade name: TMF-1.5, boiling point: 191° C., Ra: 45, viscosity: 1.4 mPa·s)

Synthesis Example 1 (Synthesis of Cationic Polymer 1)

In a reaction vessel equipped with two dropping funnels 1 and 2, monomers having a composition shown in the "Initially charged monomer solution" column of Table 1 were charged, followed by purging with a nitrogen gas.

Meanwhile, monomers and an organic solvent having a composition shown in the "Dropping monomer solution" column of Table 1 were mixed to prepare a dropping monomer solution; separately, an organic solvent and a polymerization initiator (2,2'-azobis(2,4-dimethylvaleronitrile): manufactured by Fujifilm Wako Pure Chemical Corporation, a trade name: V-65) were mixed to prepare a polymerization initiator solution; and they were charged in the dropping funnels 1 and 2, respectively, followed by purging with a nitrogen gas.

The initially charged monomer solution in the reaction vessel was kept at 62° C. in a nitrogen atmosphere while stirring, and the dropping monomer solution and the polymerization initiator solution were gradually dropped in the reaction vessel over 2 hours such that a proportion of the polymerization initiator to be dropped became constant relative to the monomers to be dropped.

After completion of dropping, the resultant was stirred for 1 hour while keeping at 62° C., and subsequently, 47 parts of acetone was added. The contents were further kept at 62° C. while stirring and thermally aged for 4 hours.

Subsequently, the unreacted monomers and the polymerization initiator residue were removed from the reaction product by using an ultrafiltration membrane (manufactured by NGK Insulators, Ltd., a ceramic-made ultrafiltration membrane, a trade name: CEFILT, pore diameter: 10 nm), and the residue was then dried to obtain a cationic amphipathic polymer (hereinafter also referred to as "cationic polymer 1"). A weight average molecular weight of the obtained cationic polymer 1 was 130,000.

Synthesis Example 2 (Synthesis of Cationic Polymer 2)

In a reaction vessel equipped with two dropping funnels 1 and 2, monomers having a composition shown in the "Initially charged monomer solution" column of Table 1 were charged, followed by purging with a nitrogen gas.

Meanwhile, monomers and an organic solvent having a composition shown in the "Dropping monomer solution" column of Table 1 were mixed to prepare a dropping monomer solution; and separately, a polymerization initiator (V-65) shown in the "Polymerization initiator solution" column of Table 1 were charged in the dropping funnels 1 and 2, respectively, followed by purging with a nitrogen gas.

The initially charged monomer solution in the reaction vessel was kept at 55° C. in a nitrogen atmosphere while stirring, and the dropping monomer solution and the polymerization initiator solution were gradually dropped in the reaction vessel over 2 hours such that a proportion of the polymerization initiator to be dropped became constant relative to the monomers to be dropped.

After completion of dropping, the contents were further kept at 55° C. while stirring and thermally aged for 5 hours.

Subsequently, the unreacted monomers and the polymerization initiator residue were removed from the reaction product by using an ultrafiltration membrane (manufactured by NGK Insulators, Ltd., a ceramic-made ultrafiltration membrane, a trade name: CEFILT, pore diameter: 10 nm), and the residue was then dried to obtain a cationic amphipathic polymer (hereinafter also referred to as "cationic polymer 2"). A weight average molecular weight of the obtained cationic polymer 2 was 120,000.

TABLE 1

|  |  | Synthesis Example 1 | | | Synthesis Example 2 | | |
| --- | --- | --- | --- | --- | --- | --- | --- |
|  |  | Reaction vessel Initially charged monomer solution | Dropping funnel 1 Dropping monomer solution | Dropping funnel 2 Polymerization initiator solution | Reaction vessel Initially charged monomer solution | Dropping funnel 1 Dropping monomer solution | Dropping funnel 2 Polymerization initiator solution |
| Monomer composition | DMAPAA *1 | 1.5 | 13.5 |  | 1.0 | 9.0 |  |
| (active ingredient) | Ethyl acrylate | 2.5 | 22.5 |  | 2.0 | 18.0 |  |
| (parts) | t-BuAAm *2 | 5.0 | 45.0 |  | 4.5 | 40.5 |  |
|  | NK ESTER M-90G *3 | 1.0 | 9.0 |  | 2.5 | 22.5 |  |
| Organic solvent | Acetone | 18.6 | 111.4 | 55.7 |  |  |  |
| (parts) | Ethanol |  |  |  | 10.0 | 60.0 | 30.0 |
| Polymerization initiator (parts) | V-65 *4 |  |  | 0.66 |  |  | 0.33 |
| Kind of cationic polymer CII-1 |  | Cationic polymer 1 | | | Cationic polymer 1 | | |
| Weight average molecular weight of cationic polymer CII-1 |  | 130,000 | | | 120,000 | | |

*1: N-[3-(Dimethylamino)propyl]acrylamide, manufactured by Sigma-Aldrich Co.
*2: N tert-Butyl acrylamide, manufactured by Sigma-Aldrich Co.
*3: Methoxypolyethylene glycol monomethacrylate, manufactured by Shin-Nakamura Chemical Co., Ltd., a trade name: NK ESTER M-90G (ethylene oxide average addition molar number = 9, end: methyl group)
*4 2,2'-Azobis(2,4-dimethylvalelonitrile), manufactured by Fujifilm Wako Pure Chemical Corporation, a trade name: V-65

Synthesis Example 3 (Synthesis of Cationic Silicone Polymer 1)

12.9 g (0.13 mol) of 2-ethyl-2-oxazoline and 27.7 g of ethyl acetate were mixed, and the mixed liquid was dehydrated with 2.0 g of a molecular sieve (ZEOLUM A-4, manufactured by Tosoh Corporation) at 28° C. for 15 hours. To the resulting dehydrated ethyl acetate solution of 2-ethyl-2-oxazoline, 0.77 g (0.005 mol) of diethyl sulfate was added, and the contents were heat-refluxed in a nitrogen atmosphere at 80° C. for 8 hours, to obtain a terminal reactive poly(N-propionylethyleneimine) (number average molecular weight: 2,700) solution.

Separately, 100.0 g of side-chain primary aminopropyl-modified polydimethylsiloxane (manufactured by Shin-Etsu Chemical Co., Ltd., a trade name: KF-8015, weight average molecular weight: 100,000 (catalogue value), amine equivalent: 20,000) and 203.0 g of ethyl acetate were mixed, and the mixed liquid was dehydrated with 15.2 g of a molecular sieve at 28° C. for 15 hours.

Subsequently, the above-obtained terminal reactive poly (N-propionylethyleneimine) solution was collectively added to the side-chain primary aminopropyl-modified polydimethylsiloxane solution, and the contents were heat-refluxed at 80° C. for 10 hours. The obtained reaction mixture was concentrated under reduced pressure to obtain a poly(N-propionylethyleneimine)/dimethylpolysiloxane copolymer (hereinafter also referred to as "cationic silicone polymer 1") as a white rubber-like solid (108 g). A weight average molecular weight of the cationic silicone polymer 1 was 115,000 (calculated value), and a mass ratio [{content of organopolysiloxane segment (x)}/[total content of {organopolysiloxane segment (x)} and {poly(N-acylalkyleneimine) segment (y)}]] was 0.87.

Synthesis Example 4 (Synthesis of Cationic Silicone Polymer 2)

53.3 g (0.54 mol) of 2-ethyl-2-oxazoline and 127.5 g of ethyl acetate were mixed, and the mixed liquid was dehydrated with 9.0 g of a molecular sieve (ZEOLUM A-4, manufactured by Tosoh Corporation) for 15 hours. To the resulting dehydrated ethyl acetate solution of 2-ethyl-2-oxazoline, 9.48 g (0.061 mol) of diethyl sulfate was added, and the contents were heat-refluxed in a nitrogen atmosphere at 80° C. for 8 hours, to obtain a terminal reactive poly(N-propionylethyleneimine) (number average molecular weight: 1,300) solution.

Separately, 153.7 g of side-chain primary aminopropyl-modified polydimethylsiloxane (manufactured by Shin-Etsu Chemical Co., Ltd., a trade name: KF-8003, weight average molecular weight: 40,000 (catalogue value), amine equivalent: 2,000) and 312.1 g of ethyl acetate were mixed, and the mixed liquid was dehydrated with 23.3 g of a molecular sieve at 28° C. for 15 hours.

Subsequently, the above-obtained terminal reactive poly (N-propionylethyleneimine) solution was collectively added to the side-chain primary aminopropyl-modified polydimethylsiloxane solution, and the contents were heat-refluxed at 80° C. for 10 hours. The reaction mixture was concentrated under reduced pressure to obtain a poly(N-propionylethyleneimine)/dimethylpolysiloxane copolymer (hereinafter also referred to as "cationic silicone polymer 2") as a pale yellow rubber-like solid (200 g). A weight average molecular weight of the cationic silicone polymer 2 was 56,000 (calculated value), and a mass ratio [{content of organopolysiloxane segment (x)}/[total content of {organopolysiloxane segment (x)} and {poly(N-acylalkyleneimine) segment (y)}]] was 0.71.

Synthesis Example 5 (Synthesis of Cationic Silicone Polymer 3)

73.7 g (0.74 mol) of 2-ethyl-2-oxazoline and 156.0 g of ethyl acetate were mixed, and the mixed liquid was dehydrated with 12.0 g of a molecular sieve (ZEOLUM A-4, manufactured by Tosoh Corporation) at 28° C. for 15 hours. To the resulting dehydrated ethyl acetate solution of 2-ethyl-2-oxazoline, 2.16 g (0.014 mol) of diethyl sulfate was added, and the contents were heat-refluxed in a nitrogen atmosphere at 80° C. for 8 hours, to obtain a terminal reactive poly(N-propionylethyleneimine) (number average molecular weight: 6,000) solution.

Separately, 70.0 g of side-chain primary aminopropyl-modified polydimethylsiloxane (a trade name: KF-864, manufactured by Shin-Etsu Silicone Co., Ltd., weight average molecular weight: 50,000 (catalogue value), amine equivalent: 3,800) and 140.0 g of ethyl acetate were mixed, and the mixed liquid was dehydrated with 15.0 g of a molecular sieve at 28° C. for 15 hours.

Subsequently, the above-obtained terminal reactive poly (N-propionylethyleneimine) solution was collectively added to the side-chain primary aminopropyl-modified polydimethylsiloxane solution, and the contents were heat-refluxed at 80° C. for 10 hours. The reaction mixture was concentrated under reduced pressure to obtain a poly(N-propionylethyleneimine)/dimethylpolysiloxane copolymer (hereinafter also referred to as "cationic silicone polymer 3") as a white rubber-like solid (135 g). A weight average molecular weight of the cationic silicone polymer 3 was 100,000 (calculated value), and a mass ratio [{content of organopolysiloxane segment (x)}/[total content of {organopolysiloxane segment (x)} and {poly(N-acylalkyleneimine) segment (y)}]] was 0.50.

Preparation Examples 1-1 to 1-5 and Comparative Preparation Examples 1-1 to 1-7

<Preparation of Liquid Composition I>

5 parts of ULTRAHOLD 8 (powder with a solid component content of 100%) and 5 parts of RAM RESIN 2000-dry as the polymer C were dissolved in the solvent A described in Table 2; after confirming that the solution was transparent and free from a floating material and a precipitate, the solvent B described in Table 2 was added; the contents were stirred and homogenized; and the resultant was filtered with a filter having a pore diameter of 0.20 μm. There were thus obtained liquid compositions I1-1 to I1-5 and I1-C1 to I1-C7. As for the used filter, from the viewpoint of solvent resistance of the filter itself, a cellulose acetate syringe filter, manufactured by Advantech Co., Ltd. was used for the liquid compositions I1-1 to I1-5, I1-C1 to I1-C2, and I1-C7, and a PTFE syringe filter, manufactured by Advantech Co., Ltd. was used for the liquid compositions I1-C3 to I1-C6.

The dissolved amount of the polymer C used in Preparation Example 1-1 in 100 g of the solvent A was 43 g, and the dissolved amount thereof in 100 g of the solvent B was 2.2 g. In addition, the dissolved amount of the polymer C used in Preparation Examples 1-2 to 1-5 in 100 g of the solvent B was less than 5 g, and the dissolved amount thereof in 100 g of the solvent A was 5 g or more.

Examples 1-1 to 1-5 and Comparative Examples 1-1 to 1-7

<Formation of Coating Film>
(Step 1: Coating Step of Liquid Composition I)

In an environmental chamber, the temperature and humidity of which were controlled at a temperature of 25° C. and a humidity of 50%, a black artificial leather (manufactured by Ideatex Japan Co., Ltd., a trade name: SUPPLALE PBZ 13001) cut into a size of 20 cm in width and 30 cm in length was fixed on a desktop coater (manufactured by Mitsui Electric Co., Ltd., a trade name: TC-1) such that the skin texture-reproduced surface became the front side. Subsequently, 5 mL of each of the liquid compositions shown in Table 2 was dropped on the skin texture-reproduced surface of the artificial leather, immediately thereafter, the respective liquid compositions were coated on the artificial leather using a No. 50 wire bar (wet film thickness T: 100 μm) at a traveling speed of 1 m/min so as to obtain a coated area of 20 mm in width and 20 cm in length.

Subsequently, in an environmental chamber, the temperature and humidity of which were controlled at a temperature of 25° C. and a humidity of 50%, the coating film formed on the artificial leather was allowed to stand for drying for 30 minutes. There were thus obtained dried polymer coating films 1-1 to 1-5 and 1-C1 to 1-C7 formed from the respective liquid compositions.

Figure 3:
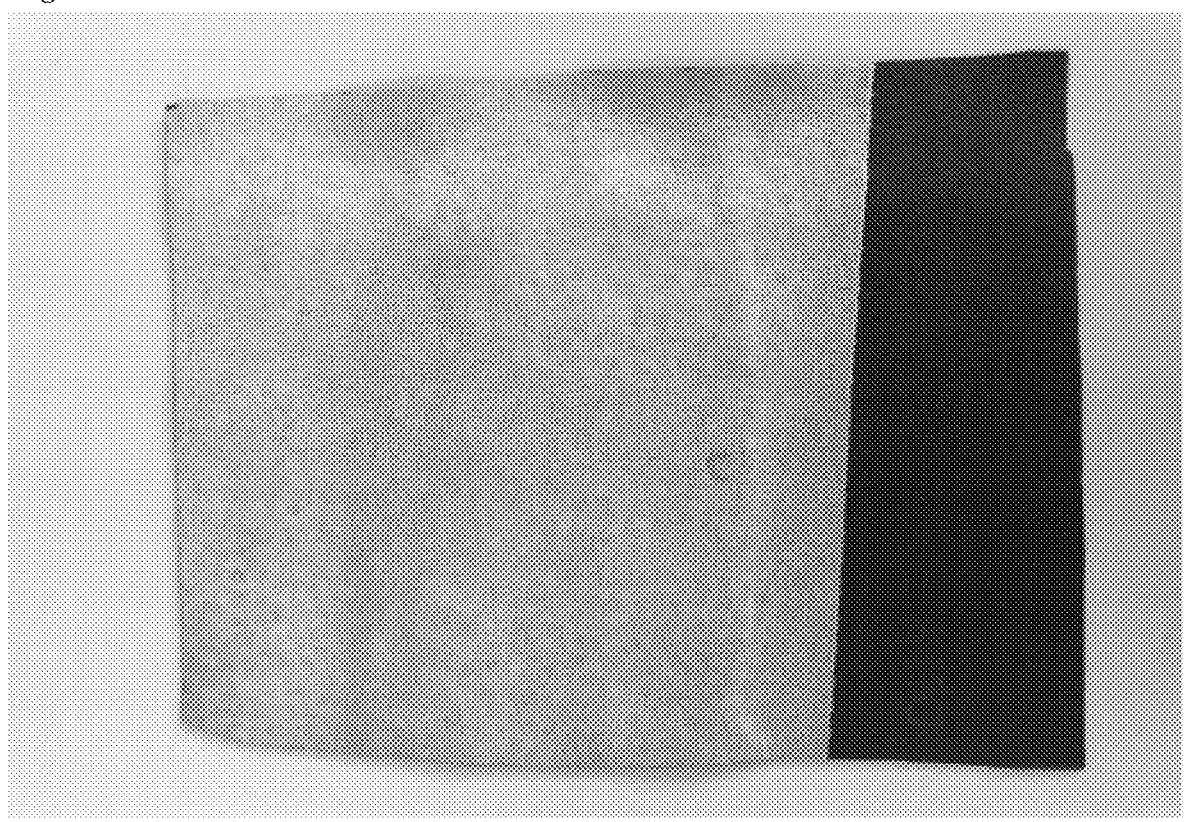
FIG. 3 is a photograph of a coating film obtained in Examples 1-1 as taken from the upper surface side.
Figure 4:
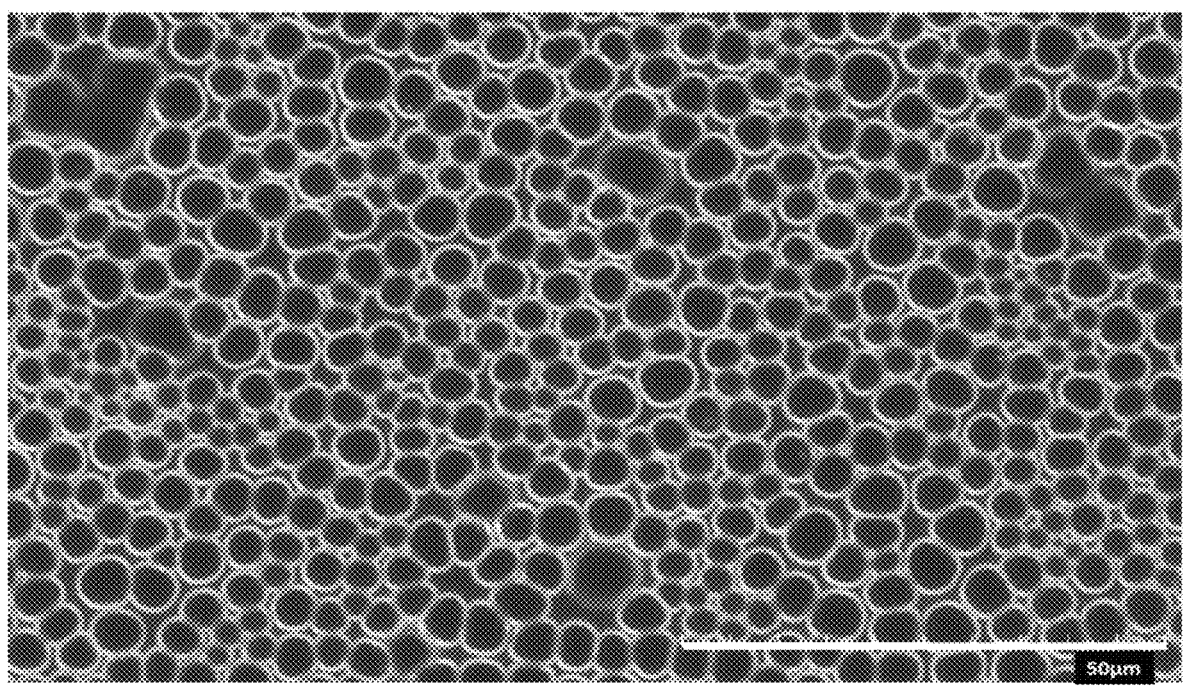
FIG. 4 is an optical microscopic photography (magnification: 2,500 times) of a coating film obtained in Examples 1-1 as taken from the upper surface side.

Here, a photograph and an optical microscopic photograph (magnification: 2,500 times) of the polymer coating film 1-1 obtained in Example 1-1 as taken from the upper surface side are shown in FIG. 3 and FIG. 4, respectively. The average particle diameter of the primary particles contained in the polymer coating film 1-1 was measured by the aforementioned method. As a result, it was found to be 4.13 μm.

<Evaluation of Concealment>

As an index of the concealment of unevenness of the skin, the image density of each of the polymer coating films obtained in the Examples and Comparative Examples was measured and evaluated regarding the whiteness. As a measuring device of the image density, a spectrophotometer/densitometer (manufactured by X-Rite, Inc., a trade name: SpectroEye) was used. The measurement condition was light source: D65, observation field: 2°, density standard: DIN, white base: "Abs", and built-in filter: "No". The results are shown in Table 2.

As a result of measurement of the image density of the non-coated glass substrate, a measured value was 1.4. It is indicated that the smaller the measured value, the higher the whiteness, and the more excellent the concealment. The measured value is preferably 1 or less, and in this case, the whiteness is high, and the concealment is excellent.

<Evaluation of Resistance to Skin Deformation>

Each of the polymer coating films obtained in the Examples and Comparative Examples was wound around a resin-made cylinder having a diameter of 3 cm and having a smooth surface such that the surface was not scraped while positioning the coating film surface inwardly and kept at ordinary temperature for 5 minutes to apply a deformation so as to compress the coating film surface, and then, the coating film was removed from the cylinder and recovered. Subsequently, the recovered coating film was evaluated according to the following criteria by observation with an optical microscope (manufactured by Hirox Co., Ltd., a trade name: RH-2000) and observation through visual inspection.

Figure 2:
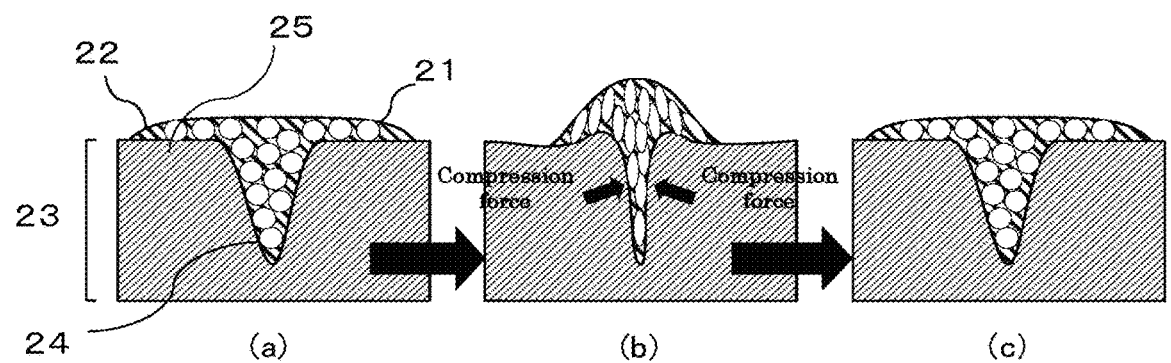
FIG. 2 is a schematic view showing one example of a cross section of a coating film formed on the skin according to a method for forming a coating film of the present invention.

In the artificial leather used in the present Examples, as shown in FIG. 2(a), a structure of crista cutis and sulcus cutis close to the skin texture of the human body is provided, and the polymer film is formed extending from the bottom of the sulcus cutis to the crista cutis. Then, in the case where the skin contracts, as shown in FIG. 2(b), the polymer film taken into the sulcus cutis portion is compressed. For that reason, by applying a deformation of compressing the coating film surface as in the aforementioned method and then observing the state of the coating film after releasing the compression force, the resistance to skin deformation can be evaluated. The case where the score is 3 or more according to the following evaluation criteria is not practically problematic. The results are shown in Table 2.

[Evaluation Criteria]

5: In all of the optical microscopic observation and the visual observation, any change was not seen at all on the coating film surface, and the coating film surface was kept in a favorable state.

4: In the optical microscopic observation, a deformed mark was seen in a part of the coating film surface, but in the visual inspection, the change was not substantially confirmed on the coating film surface.

3: In the optical microscopic observation, a deformed mark or white discoloration was seen on the coating film surface of the sulcus cutis portion of the base material, but in the visual inspection, the deformation of the coating film was not confirmed.

2: In the optical microscopic observation, the coating film surface on the sulcus cutis portion of the base material was deformed, and the coating film was pushed outside of the sulcus cutis, and in the visual inspection, deformation of the coating film was conformed, too.

1: In the optical microscopic observation, the coating film surface on the sulcus cutis portion of the base material was deformed, and the coating film of the sulcus cutis portion was peeled off, and the desquamation was generated.

<Evaluation of Foundation Adherence>

On the surface of each of the polymer coating films obtained in the Examples and Comparative Examples, a liquid foundation (manufactured by Kao Corporation, a trade name: SOFINA PRIMAVISTA BEIGE OCHRE 03) was coated using an attached sponge. The coating amount was adjusted by changing the coating amount of the liquid foundation for every coating film as in the "Image density after foundation (hereinafter also referred to as "FD") coating" described in Table 2.

As a measuring device of the image density, a spectrophotometer/densitometer (manufactured by X-Rite, Inc., a trade name: SpectroEye) was used. The measurement condition was light source: D65, observation field: 2°, density standard: DIN, white base: "Abs", and built-in filter: "No".

Subsequently, the polymer coating film was wound around a resin-made cylinder having a diameter of 3 cm and having a smooth surface such that the surface was not scraped while positioning the coating film surface inwardly and kept at ordinary temperature for 5 minutes to apply a deformation so as to compress the coating film surface, and then, the coating film was removed from the cylinder and recovered.

Subsequently, the surface on which the FD of the recovered coating film was scraped with a cellulose-made nonwoven fabric (manufactured by Ozu Corporation, a trade name: BEMCOT® LINT-FREE PS-2) at a surface pressure of 10 g/cm$^2$ so as to make 10 reciprocations. Subsequently, the image density of the scraped place was measured in the same manner as mentioned above and defined as "Image density after foundation (FD) scraping".

Subsequently, a difference (image density difference before and after FD scraping (amount in change of image density)) between the "Image density of after FD coating" and the "Image density after FD scraping" was determined to evaluate the FD adherence. The smaller the image density difference before and after FD scraping", the more excellent the FD adherence. The foregoing difference is preferably 0.6 or less, more preferably 0.3 or less, and still more preferably 0.1 or less. The results are shown in Table 2.

TABLE 2

| | | | | | Example | | | | Comparative Example | | |
|---|---|---|---|---|---|---|---|---|---|---|---|
| | | | | | 1-1 | 1-2 | 1-3 | 1-4 | 1-1 | 1-2 | 1-3 |
| Liquid composition I No. | | | | | I1-1 | I1-2 | I1-3 | I1-4 | I1-C1 | I1-C2 | I1-C3 |
| Composition (parts) | Solvent A | Kind | Boiling point (° C.) | Ra | | | | | | | |
| | | Ethanol | 78 | 24 | 70 | | | | | | |
| | | Propanol | 97 | 27 | | 70 | | | | | |
| | | Isopropanol | 82 | 28 | | | 70 | | | | |
| | | tert-Butyl alcohol | 82 | 30 | | | | 70 | | | |
| | | Butanol | 118 | 28 | | | | | 70 | | |
| | | Pentanol | 138 | 30 | | | | | | 70 | |
| | | Chloroform | 61 | 39 | | | | | | | 70 |
| | | Toluene | 111 | 43 | | | | | | | |
| | Solvent B | Kind | Boiling point (° C.) | Ra | | | | | | | |
| | | PARLEAM 3 | 179 | 45 | 20 | 20 | 20 | 20 | 20 | 20 | 20 |
| | | Isododecane | 177 | 45 | | | | | | | |
| | | Hexane | 69 | 45 | | | | | | | |
| | | Dimethylformamide | 153 | 31 | | | | | | | |
| | Polymer C | ULTRAHOLD 8 | | | 5 | 5 | 5 | 5 | 5 | 5 | 5 |
| | | RAM RESIN 2000-dry | | | 5 | 5 | 5 | 5 | 5 | 5 | 5 |
| Viscosity of liquid composition I (mPa · s) | | | | | 10.2 | 20.3 | 15.6 | 12.9 | 32.8 | 72.8 | 35.2 |
| Base material | | | | | SUPPLALE | | | | | | |
| Wet film thickness T (μm) | | | | | 100 | 100 | 100 | 100 | 100 | 100 | 100 |
| Evaluation | Coating film No. | | | | 1-1 | 1-2 | 1-3 | 1-4 | 1-C1 | 1-C2 | 1-C3 |
| | Whiteness (image density) | Coating film | | | 0.49 | 0.81 | 0.75 | 0.63 | 1.41 | 1.44 | 1.35 |
| | | After FD coating | | | 0.40 | 0.40 | 0.40 | 0.40 | 0.40 | 0.40 | 0.40 |
| | | After FD scraping | | | 0.43 | 0.50 | 0.49 | 0.48 | 1.12 | 1.14 | 1.09 |
| | Amount in change of image density before and after FD scraping | | | | 0.03 | 0.10 | 0.09 | 0.08 | 0.72 | 0.74 | 0.69 |
| | Resistance to skin deformation | | | | 4 | 4 | 4 | 4 | 2 | 2 | 1 |

| | | | | | Comparative Example | Example | Comparative Example | | |
|---|---|---|---|---|---|---|---|---|---|
| | | | | | 1-4 | 1-5 | 1-5 | 1-6 | 1-7 |
| Liquid composition I No. | | | | | I1-C4 | I1-5 | I1-C5 | I1-C6 | I1-C7 |
| Composition (parts) | Solvent A | Kind | Boiling point (° C.) | Ra | | | | | |
| | | Ethanol | 78 | 24 | | 70 | 70 | 70 | 90 |
| | | Propanol | 97 | 27 | | | | | |
| | | Isopropanol | 82 | 28 | | | | | |
| | | tert-Butyl alcohol | 82 | 30 | | | | | |

TABLE 2-continued

|  |  |  | Butanol | 118 | 28 |  |  |  |  |  |
|---|---|---|---|---|---|---|---|---|---|---|
|  |  |  | Pentanol | 138 | 30 |  |  |  |  |  |
|  |  |  | Chloroform | 61 | 39 |  |  |  |  |  |
|  |  |  | Toluene | 111 | 43 | 70 |  |  |  |  |
|  | Solvent | Kind |  | Boiling point (° C.) | Ra |  |  |  |  |  |
|  | B |  | PARLEAM 3 | 179 | 45 | 20 |  |  |  |  |
|  |  |  | Isododecane | 177 | 45 |  | 20 |  |  |  |
|  |  |  | Hexane | 69 | 45 |  |  | 20 |  |  |
|  |  |  | Dimethylformamide | 153 | 31 |  |  |  | 20 |  |
|  | Polymer | ULTRAHOLD 8 |  |  |  | 5 | 5 | 5 | 5 | 5 |
|  | C | RAM RESIN 2000-dry |  |  |  | 5 | 5 | 5 | 5 | 5 |
| Viscosity of liquid composition I (mPa · s) |  |  |  |  |  | 5.7 | 9.8 | 8.6 | 8.5 | 8.3 |
| Base material |  |  |  |  |  | SUPPLALE |  |  |  |  |
| Wet film thickness T (μm) |  |  |  |  |  | 100 | 100 | 100 | 100 | 100 |
| Evaluation |  | Coating film No. |  |  |  | 1-C4 | 1-5 | 1-C5 | 1-C6 | 1-C7 |
|  |  | Whiteness | Coating film |  |  | 1.30 | 0.65 | 1.36 | 1.40 | 1.39 |
|  |  | (image | After FD coating |  |  | 0.40 | 0.40 | 0.40 | 0.40 | 0.40 |
|  |  | density) | After FD scraping |  |  | 1.11 | 0.48 | 1.08 | 1.17 | 1.19 |
|  |  | Amount in change of image density before and after FD scraping |  |  |  | 0.71 | 0.08 | 0.68 | 0.77 | 0.79 |
|  |  | Resistance to skin deformation |  |  |  | 1 | 4 | 2 | 2 | 1 |

From Table 2, in view of the fact that the coating films 1-1 to 1-5 obtained in Examples 1-1 to 1-5 are high in the whiteness, exhibit high concealment even without containing an inorganic pigment, and are excellent in the resistance to skin deformation, and therefore, it is noted that they are excellent in the makeup durability. In addition, even in the case of being scraped after the FD coating, it is noted that these coating films are able to keep the high whiteness and are also excellent in the FD adherence.

On the other hand, it is noted that the coating films 1-C1 to 1-C7 obtained in Comparative Examples 1-1 to 1-7 are high in the transparency because they are low in the whiteness, and they do not express the desired concealment and are inferior in the resistance to skin deformation. In addition, in the case of being scraped after the FD coating, it is noted that these coating films are also inferior in the FD adherence because the whiteness is lowered.

Examples 2-1 to 2-5 and Comparative Examples 2-1 to 1-7

<Formation of Coating Film>

(Step 1: Coating Step of Liquid Composition I)

Each of the liquid compositions shown in Table 3 was coated on the aforementioned artificial leather (SUPPLALE) in the same manner as in the step 1 of Example 1-1.

(Step 2: Droplet-Applying Step)

During an interval of 3 to 5 seconds after coating the respective liquid compositions, ion-exchanged water was atomized on the coating film formed on the artificial leather for 5 seconds by using an ultrasonic nebulizer (manufactured by OMRON Corporation, a trade name: OMRON NE-U12) (atomizing capacity: 3 mL/min, average particle diameter of atomized droplet: 1 to 5 μm (all of which are a catalogue value)) (hereinafter also referred to as "atomizer A").

Subsequently, in an environmental chamber, the temperature and humidity of which were controlled at a temperature of 25° C. and a humidity of 50%, the coating film having the droplets applied thereto was allowed to stand for drying for 30 minutes. There were thus obtained dried polymer coating films 2-1 to 2-5 and 2-C1 to 2-C7 formed from the respective liquid compositions.

Figure 5:
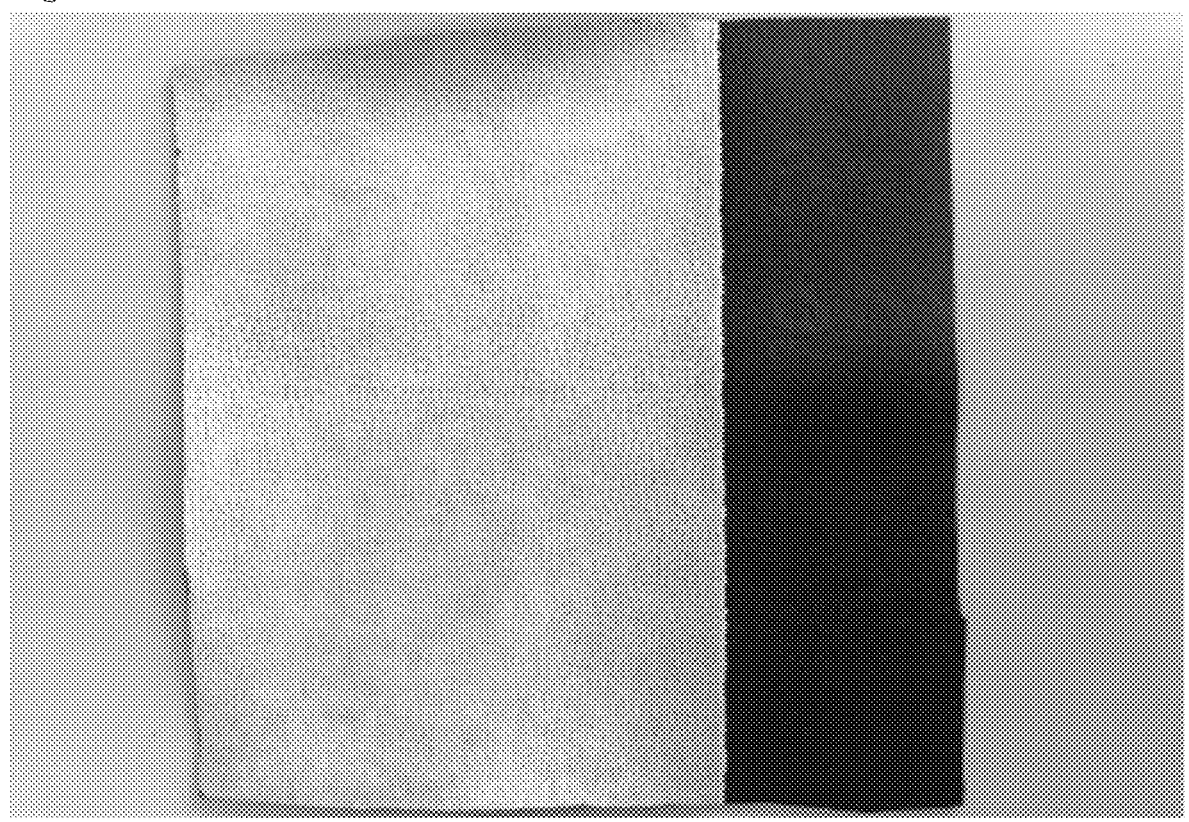
FIG. 5 is a photograph of a coating film obtained in Examples 2-1 as taken from the upper surface side.
Figure 6:
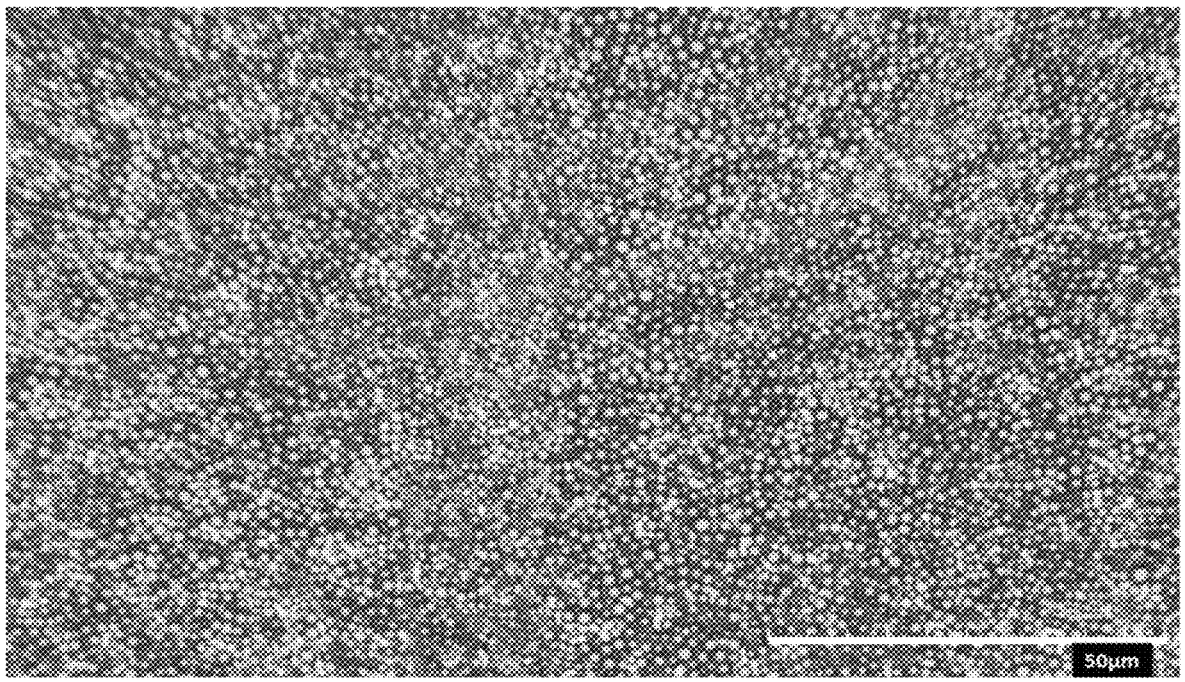
FIG. 6 is an optical microscopic photography (magnification: 2,500 times) of a coating film obtained in Examples 2-1 as taken from the upper surface side.

Here, a photograph and an optical microscopic photograph (magnification: 2,500 times) of the polymer coating film 2-1 obtained in Example 2-1 as taken from the upper surface side are shown in FIG. 5 and FIG. 6, respectively. The average particle diameter of the primary particles contained in the polymer coating film 2-1 was measured by the aforementioned method. As a result, it was found to be 0.76 μm.

Subsequently, the concealment, the resistance to skin deformation, and the FD adherence were evaluated in the same manners as mentioned above. The results are shown in Table 3.

TABLE 3

|  |  |  |  |  |  | Example |  |  |  | Comparative Example |  |  |
|---|---|---|---|---|---|---|---|---|---|---|---|---|
|  |  |  |  |  |  | 2-1 | 2-2 | 2-3 | 2-4 | 2-1 | 2-2 | 2-3 |
| Step 1 | Liquid composition I No. |  |  |  |  | I1-1 | I1-2 | I1-3 | I1-4 | I1-C1 | I1-C2 | I1-C3 |
|  | Composition (parts) | Solvent A | Kind | Boiling point (° C.) | Ra |  |  |  |  |  |  |  |
|  |  |  | Ethanol | 78 | 24 | 70 |  |  |  |  |  |  |
|  |  |  | Propanol | 97 | 27 |  | 70 |  |  |  |  |  |
|  |  |  | Isopropanol | 82 | 28 |  |  | 70 |  |  |  |  |
|  |  |  | tert-Butyl alcohol | 82 | 30 |  |  |  | 70 |  |  |  |
|  |  |  | Butanol | 118 | 28 |  |  |  |  | 70 |  |  |
|  |  |  | Pentanol | 138 | 30 |  |  |  |  |  | 70 |  |
|  |  |  | Chloroform | 61 | 39 |  |  |  |  |  |  | 70 |
|  |  |  | Toluene | 111 | 43 |  |  |  |  |  |  |  |
|  |  | Solvent B | Kind | Boiling point (° C.) | Ra |  |  |  |  |  |  |  |
|  |  |  | PARLEAM 3 | 179 | 45 | 20 | 20 | 20 | 20 | 20 | 20 | 20 |
|  |  |  | Isododecane | 177 | 45 |  |  |  |  |  |  |  |

TABLE 3-continued

| | | | | | | | | | | | | |
|---|---|---|---|---|---|---|---|---|---|---|---|---|
| | | | Hexane | | 69 | 45 | | | | | | |
| | | | Dimethylformamide | | 153 | 31 | | | | | | |
| | | Polymer | ULTRAHOLD 8 | | | | 5 | 5 | 5 | 5 | 5 | 5 | 5 |
| | | C | RAM RESIN 2000-dry | | | | 5 | 5 | 5 | 5 | 5 | 5 | 5 |
| | Viscosity of liquid composition I (mPa·s) | | | | | | 10.2 | 20.3 | 15.6 | 12.9 | 32.8 | 72.8 | 35.2 |
| | Base material | | | | | | | | | SUPPLALE | | | |
| | Wet film thickness T (μm) | | | | | | 100 | 100 | 100 | 100 | 100 | 100 | 100 |
| Step 2 | Kind of atomizer | | | | | | A | A | A | A | A | A | A |
| | Atomizing time (sec) | | | | | | 5 | 5 | 5 | 5 | 5 | 5 | 5 |
| | Average particle diameter of atomized droplets (μm) | | | | | | | | | 1 to 5 | | | |
| Evaluation | Coating film No. | | | | | | 2-1 | 2-2 | 2-3 | 2-4 | 2-C1 | 2-C2 | 2-C3 |
| | White ness | Coating film | | | | | 0.32 | 0.71 | 0.54 | 0.42 | 1.39 | 1.42 | 1.28 |
| | (image | After FD coating | | | | | 0.30 | 0.30 | 0.30 | 0.30 | 0.30 | 0.30 | 0.30 |
| | density) | After FD scraping | | | | | 0.30 | 0.37 | 0.35 | 0.33 | 1.11 | 1.15 | 1.08 |
| | Amount in change of image density before and after FD scraping | | | | | | 0.00 | 0.07 | 0.05 | 0.03 | 0.81 | 0.85 | 0.78 |
| | Resistance to skin deformation | | | | | | 5 | 5 | 5 | 5 | 2 | 2 | 1 |

| | | | | | | | Comparative Example | Example | Comparative Example | | |
|---|---|---|---|---|---|---|---|---|---|---|---|
| | | | | | | | 2-4 | 2-5 | 2-5 | 2-6 | 2-7 |
| Step 1 | Liquid composition I No. | | | | | | I1-C4 | I1-5 | I1-C5 | I1-C6 | I1-C7 |
| | Composition (parts) | Solvent A | Kind | Boiling point (°C.) | Ra | | | | | | |
| | | | Ethanol | 78 | 24 | | | 70 | 70 | 70 | 90 |
| | | | Propanol | 97 | 27 | | | | | | |
| | | | Isopropanol | 82 | 28 | | | | | | |
| | | | tert-Butyl alcohol | 82 | 30 | | | | | | |
| | | | Butanol | 118 | 28 | | | | | | |
| | | | Pentanol | 138 | 30 | | | | | | |
| | | | Chloroform | 61 | 39 | | | | | | |
| | | | Toluene | 111 | 43 | | 70 | | | | |
| | | Solvent B | Kind | Boiling point (°C.) | Ra | | | | | | |
| | | | PARLEAM 3 | 179 | 45 | | 20 | | | | |
| | | | Isododecane | 177 | 45 | | | 20 | | | |
| | | | Hexane | 69 | 45 | | | | 20 | | |
| | | | Dimethylformamide | 153 | 31 | | | | | 20 | |
| | | Polymer | ULTRAHOLD 8 | | | | 5 | 5 | 5 | 5 | 5 |
| | | C | RAM RESIN 2000-dry | | | | 5 | 5 | 5 | 5 | 5 |
| | Viscosity of liquid composition I (mPa·s) | | | | | | 5.7 | 9.8 | 8.6 | 8.5 | 8.3 |
| | Base material | | | | | | | | SUPPLALE | | |
| | Wet film thickness T (μm) | | | | | | 100 | 100 | 100 | 100 | 100 |
| Step 2 | Kind of atomizer | | | | | | A | A | A | A | A |
| | Atomizing time (sec) | | | | | | 5 | 5 | 5 | 5 | 5 |
| | Average particle diameter of atomized droplets (μm) | | | | | | | | 1 to 5 | | |
| Evaluation | Coating film No. | | | | | | 2-C4 | 2-5 | 2-C5 | 2-C6 | 2-C7 |
| | White ness | Coating film | | | | | 1.26 | 0.45 | 1.32 | 1.34 | 1.35 |
| | (image | After FD coating | | | | | 0.30 | 0.30 | 0.30 | 0.30 | 0.30 |
| | density) | After FD scraping | | | | | 1.09 | 0.32 | 1.09 | 1.18 | 1.18 |
| | Amount in change of image density before and after FD scraping | | | | | | 0.79 | 0.02 | 0.79 | 0.88 | 0.88 |
| | Resistance to skin deformation | | | | | | 1 | 5 | 2 | 2 | 1 |

From Table 3, in view of the fact that the coating films 2-1 to 2-5 obtained in Examples 2-1 to 2-5 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

On the other hand, it is noted that the coating films 2-C1 to 2-C7 obtained in Comparative Examples 2-1 to 2-7 are high in the transparency because they are low in the whiteness, and they do not express the desired concealment and are inferior in the resistance to skin deformation. In addition, in the case of being scraped after the FD coating, it is noted that these coating films are also inferior in the FD adherence because the whiteness is lowered.

Examples 3-1 to 3-5 and Comparative Examples 3-1 to 3-7

<Formation of Coating Film>
(Step 1: Coating Step of Liquid Composition I)
Each of the liquid compositions shown in Table 4 was coated on the aforementioned artificial leather (SUPPLALE) in the same manner as in the step 1 of Example 1-1.

(Step 2: Droplet-Applying Step)
During an interval of 3 to 5 seconds after coating the respective liquid compositions, ion-exchanged water was atomized on the coating film formed on the artificial leather for 5 seconds by using a jet nebulizer (manufactured by Alfresa Pharma Corporation, a trade name: NESCOJET AZ-11) (atomizing capacity: 0.5 to 0.6 mL/min, average particle diameter of atomized droplet: 5 to 15 μm (all of which are a catalogue value)) (hereinafter also referred to as "atomizer B").

Subsequently, in an environmental chamber, the temperature and humidity of which were controlled at a temperature of 25° C. and a humidity of 50%, the coating film having the droplets applied thereto was allowed to stand for drying for 30 minutes. There were thus obtained dried polymer coating films 3-1 to 3-5 and 3-C1 to 3-C7 formed from the respective liquid compositions.

Subsequently, the concealment, the resistance to skin deformation, and the FD adherence were evaluated in the same manners as mentioned above. The results are shown in Table 4.

TABLE 4

|  |  |  |  |  |  | Example | | | | Comparative Example | | |
|---|---|---|---|---|---|---|---|---|---|---|---|---|
|  |  |  |  |  |  | 3-1 | 3-2 | 3-3 | 3-4 | 3-1 | 3-2 | 3-3 |
| Step 1 | Liquid composition I No. |  |  |  |  | I1-1 | I1-2 | I1-3 | I1-4 | I1-C1 | I1-C2 | I1-C3 |
|  | Composition (parts) | Solvent A | Kind | Boiling point (° C.) | Ra |  |  |  |  |  |  |  |
|  |  |  | Ethanol | 78 | 24 | 70 |  |  |  |  |  |  |
|  |  |  | Propanol | 97 | 27 |  | 70 |  |  |  |  |  |
|  |  |  | Isopropanol | 82 | 28 |  |  | 70 |  |  |  |  |
|  |  |  | tert-Butyl alcohol | 82 | 30 |  |  |  | 70 |  |  |  |
|  |  |  | Butanol | 118 | 28 |  |  |  |  | 70 |  |  |
|  |  |  | Pentanol | 138 | 30 |  |  |  |  |  | 70 |  |
|  |  |  | Chloroform | 61 | 39 |  |  |  |  |  |  | 70 |
|  |  |  | Toluene | 111 | 43 |  |  |  |  |  |  |  |
|  |  | Solvent B | Kind | Boiling point (° C.) | Ra |  |  |  |  |  |  |  |
|  |  |  | PARLEAM 3 | 179 | 45 | 20 | 20 | 20 | 20 | 20 | 20 | 20 |
|  |  |  | Isododecane | 177 | 45 |  |  |  |  |  |  |  |
|  |  |  | Hexane | 69 | 45 |  |  |  |  |  |  |  |
|  |  |  | Dimethylformamide | 153 | 31 |  |  |  |  |  |  |  |
|  |  | Polymer C | ULTRAHOLD 8 |  |  | 5 | 5 | 5 | 5 | 5 | 5 | 5 |
|  |  |  | RAM RESIN 2000-dry |  |  | 5 | 5 | 5 | 5 | 5 | 5 | 5 |
|  | Viscosity of liquid composition I (mPa · s) |  |  |  |  | 10.2 | 20.3 | 15.6 | 12.9 | 32.8 | 72.8 | 35.2 |
|  | Base material |  |  |  |  | SUPPLALE | | | | | | |
|  | Wet film thickness T (μm) |  |  |  |  | 100 | 100 | 100 | 100 | 100 | 100 | 100 |
| Step 2 | Kind of atomizer |  |  |  |  | B | B | B | B | B | B | B |
|  | Atomizing time (sec) |  |  |  |  | 5 | 5 | 5 | 5 | 5 | 5 | 5 |
|  | Average particle diameter of atomized droplets (μm) |  |  |  |  | 5 to 15 | | | | | | |
| Evaluation | Coating film No. |  |  |  |  | 3-1 | 3-2 | 3-3 | 3-4 | 3-C1 | 3-C2 | 3-C3 |
|  | White ness (image density) | Coating film |  |  |  | 0.39 | 0.72 | 0.58 | 0.44 | 1.39 | 1.42 | 1.30 |
|  |  | After FD coating |  |  |  | 0.30 | 0.30 | 0.30 | 0.30 | 0.30 | 0.30 | 0.30 |
|  |  | After FD scraping |  |  |  | 0.31 | 0.36 | 0.35 | 0.33 | 1.12 | 1.16 | 1.10 |
|  | Amount in change of image density before and after FD scraping |  |  |  |  | 0.01 | 0.06 | 0.05 | 0.03 | 0.82 | 0.86 | 0.80 |
|  | Resistance to skin deformation |  |  |  |  | 5 | 5 | 5 | 5 | 2 | 2 | 1 |

|  |  |  |  |  |  | Comparative Example | Example | Comparative Example | | |
|---|---|---|---|---|---|---|---|---|---|---|
|  |  |  |  |  |  | 3-4 | 3-5 | 3-5 | 3-6 | 3-7 |
| Step 1 | Liquid composition I No. |  |  |  |  | I1-C4 | I1-5 | I1-C5 | I1-C6 | I1-C7 |
|  | Composition (parts) | Solvent A | Kind | Boiling point (° C.) | Ra |  |  |  |  |  |
|  |  |  | Ethanol | 78 | 24 |  | 70 | 70 | 70 | 90 |
|  |  |  | Propanol | 97 | 27 |  |  |  |  |  |
|  |  |  | Isopropanol | 82 | 28 |  |  |  |  |  |
|  |  |  | tert-Butyl alcohol | 82 | 30 |  |  |  |  |  |
|  |  |  | Butanol | 118 | 28 |  |  |  |  |  |
|  |  |  | Pentanol | 138 | 30 |  |  |  |  |  |
|  |  |  | Chloroform | 61 | 39 |  |  |  |  |  |
|  |  |  | Toluene | 111 | 43 | 70 |  |  |  |  |
|  |  | Solvent B | Kind | Boiling point (° C.) | Ra |  |  |  |  |  |
|  |  |  | PARLEAM 3 | 179 | 45 | 20 |  |  |  |  |
|  |  |  | Isododecane | 177 | 45 |  | 20 |  |  |  |
|  |  |  | Hexane | 69 | 45 |  |  | 20 |  |  |
|  |  |  | Dimethylformamide | 153 | 31 |  |  |  | 20 |  |
|  |  | Polymer C | ULTRAHOLD 8 |  |  | 5 | 5 | 5 | 5 | 5 |
|  |  |  | RAM RESIN 2000-dry |  |  | 5 | 5 | 5 | 5 | 5 |
|  | Viscosity of liquid composition I (mPa · s) |  |  |  |  | 5.7 | 9.8 | 8.6 | 8.5 | 8.3 |
|  | Base material |  |  |  |  |  | SUPPLALE | | | |
|  | Wet film thickness T (μm) |  |  |  |  | 100 | 100 | 100 | 100 | 100 |
| Step 2 | Kind of atomizer |  |  |  |  | B | B | B | B | B |
|  | Atomizing time (sec) |  |  |  |  | 5 | 5 | 5 | 5 | 5 |
|  | Average particle diameter of atomized droplets (μm) |  |  |  |  | 5 to 15 | | | | |
| Evaluation | Coating film No. |  |  |  |  | 3-C4 | 3-5 | 3-C5 | 3-C6 | 3-C7 |
|  | White ness (image density) | Coating film |  |  |  | 1.27 | 0.52 | 1.33 | 1.35 | 1.36 |
|  |  | After FD coating |  |  |  | 0.30 | 0.30 | 0.30 | 0.30 | 0.30 |
|  |  | After FD scraping |  |  |  | 1.10 | 0.34 | 1.11 | 1.17 | 1.17 |

TABLE 4-continued

| | | | | | |
|---|---|---|---|---|---|
| Amount in change of image density before and after FD scraping | 0.80 | 0.04 | 0.81 | 0.87 | 0.87 |
| Resistance to skin deformation | 1 | 5 | 2 | 2 | 1 |

From Table 4, in view of the fact that the coating films 3-1 to 3-5 obtained in Examples 3-1 to 3-5 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

On the other hand, it is noted that the coating films 3-C1 to 3-C7 obtained in Comparative Examples 3-1 to 3-7 are high in the transparency because they are low in the whiteness, and they do not express the desired concealment and are inferior in the resistance to skin deformation. In addition, in the case of being scraped after the FD coating, it is noted that these coating films are also inferior in the FD adherence because the whiteness is lowered.

Preparation Examples 4-1 to 4-15

<Preparation of Liquid Composition I>

Each of the polymers C shown in Table 5 was dissolved in absolute ethanol as the solvent A; after confirming that the solution was transparent and free from a floating material and a precipitate, PARLEAM 3 was added as the solvent B; the contents were stirred and homogenized; and the resultant was filtered with a cellulose acetate syringe filter having a pore diameter of 0.20 μm, manufactured by Advantech Co., Ltd. There were thus obtained liquid compositions I4-1 to I4-15.

The dissolved amount of each of the polymers C used in Preparation Examples 4-1 to 4-15 in 100 g of the solvent B was less than 5 g, and the dissolved amount thereof in 100 g of the solvent A was 5 g or more.

Examples 4-1 to 4-15

<Formation of Coating Film>

Dried polymer coating films 4-1 to 4-15 were obtained in the same manner as in Example 2-1, except for changing the liquid composition I1-1 to each of the liquid compositions as shown in Table 5.

Subsequently, the concealment, the resistance to skin deformation, and the FD adherence were evaluated in the same manners as mentioned above. The results are shown in Table 5.

TABLE 5

| | | | | | Example | | | | | | | |
|---|---|---|---|---|---|---|---|---|---|---|---|---|
| | | | | | 4-1 | 4-2 | 4-3 | 4-4 | 4-5 | 4-6 | 4-7 | 4-8 |
| Step 1 | Liquid composition I No. | | | | I4-1 | I4-2 | I4-3 | I4-4 | I4-5 | I4-6 | I4-7 | I4-8 |
| | Composition (parts) | Solvent A | | Ethanol | 70 | 70 | 70 | 70 | 70 | 70 | 70 | 70 |
| | | Solvent B | | PARLEAM 3 | 20 | 20 | 20 | 20 | 20 | 20 | 20 | 20 |
| | | Polymer C | Anionic polymer CI | ULTRAHOLD 8 | | 10 | | | | | 5 | |
| | | | | ULTRAHOLD STRONG | | | 10 | | | | | 5 |
| | | | | ULTRAHOLD POWER-dry | | | | 10 | | | | |
| | | | Cationic polymer CII-1 | Cationic polymer 1 | | | | | 10 | | | |
| | | | | Cationic polymer 2 | | | | | | 10 | | |
| | | | Betaine polymer CIII | YUKA FORMER SM-dry | 10 | | | | | | 5 | 5 |
| | | | | RAM RESIN 1000-dry | | | | | | | | |
| | | | | RAM RESIN 2000-dry | | | | | | | | |
| | | | | RAM RESIN 4000-dry | | | | | | | | |
| | Viscosity of liquid composition I (mPa · s) | | | | 16.2 | 7.3 | 12.8 | 25.3 | 42.5 | 61.3 | 30.4 | 175.0 |
| | Base material | | | | | | | SUPPLALE | | | | |
| | Wet film thickness T (μm) | | | | 100 | 100 | 100 | 100 | 100 | 100 | 100 | 100 |
| Step 2 | Kind of atomizer | | | | A | A | A | A | A | A | A | A |
| | Atomizing time (sec) | | | | 5 | 5 | 5 | 5 | 5 | 5 | 5 | 5 |
| | Average particle diameter of atomized droplets (μm) | | | | | | | 1 to 5 | | | | |
| Evaluation | Coating film No. | | | | 4-1 | 4-2 | 4-3 | 4-4 | 4-5 | 4-6 | 4-7 | 4-8 |
| | Whiteness (image density) | Coating film | | | 0.44 | 0.68 | 0.75 | 0.72 | 0.64 | 0.63 | 0.21 | 0.32 |
| | | After FD coating | | | 0.30 | 0.30 | 0.30 | 0.30 | 0.30 | 0.30 | 0.30 | 0.30 |
| | | After FD scraping | | | 0.34 | 0.40 | 0.45 | 0.42 | 0.40 | 0.39 | 0.30 | 0.30 |
| | Amount in change of image density before and after FD scraping | | | | 0.04 | 0.10 | 0.15 | 0.12 | 0.10 | 0.09 | 0.00 | 0.00 |
| | Resistance to skin deformation | | | | 5 | 5 | 5 | 5 | 5 | 5 | 5 | 5 |

TABLE 5-continued

|  |  |  |  | Example | | | | | | |
|---|---|---|---|---|---|---|---|---|---|---|
|  |  |  |  | 4-9 | 4-10 | 4-11 | 4-12 | 4-13 | 4-14 | 4-15 |
| Step 1 | Liquid composition I No. |  |  | I4-9 | I4-10 | I4-11 | I4-12 | I4-13 | I4-14 | I4-15 |
|  | Composition (parts) | Solvent A | Ethanol | 70 | 70 | 70 | 70 | 70 | 70 | 70 |
|  |  | Solvent B | PARLEAM 3 | 20 | 20 | 20 | 20 | 20 | 20 | 20 |
|  |  | Polymer C Anionic polymer CI | ULTRAHOLD 8 |  |  |  | 5 | 5 | 5 | 5 |
|  |  |  | ULTRAHOLD STRONG |  |  |  | 5 |  |  |  |
|  |  |  | ULTRAHOLD POWER-dry | 5 |  |  |  |  |  |  |
|  |  | Cationic polymer CII-1 | Cationic polymer 1 |  | 5 |  |  |  |  |  |
|  |  |  | Cationic polymer 2 |  |  | 5 |  |  |  |  |
|  |  | Betaine polymer CIII | YUKA FORMER SM-dry | 5 | 5 | 5 |  |  |  |  |
|  |  |  | RAM RESIN 1000-dry |  |  |  |  | 5 |  |  |
|  |  |  | RAM RESIN 2000-dry |  |  |  |  |  | 5 |  |
|  |  |  | RAM RESIN 4000-dry |  |  |  |  |  |  | 5 |
|  | Viscosity of liquid composition I (mPa · s) |  |  | 29.9 | 18.3 | 19.2 | 9.9 | 27.6 | 10.2 | 23.7 |
|  | Base material |  |  | SUPPLALE | | | | | | |
|  | Wet film thickness T (μm) |  |  | 100 | 100 | 100 | 100 | 100 | 100 | 100 |
| Step 2 | Kind of atomizer |  |  | A | A | A | A | A | A | A |
|  | Atomizing time (sec) |  |  | 5 | 5 | 5 | 5 | 5 | 5 | 5 |
|  | Average particle diameter of atomized droplets (μm) |  |  | 1 to 5 | | | | | | |
| Evaluation | Coating film No. |  |  | 4-9 | 4-10 | 4-11 | 4-12 | 4-13 | 4-14 | 4-15 |
|  | Whiteness (image density) | Coating film |  | 0.54 | 0.43 | 0.33 | 0.63 | 0.63 | 0.32 | 0.66 |
|  |  | After FD coating |  | 0.30 | 0.30 | 0.30 | 0.30 | 0.30 | 0.30 | 0.30 |
|  |  | After FD scraping |  | 0.36 | 0.33 | 0.30 | 0.39 | 0.36 | 0.30 | 0.35 |
|  | Amount in change of image density before and after FD scraping |  |  | 0.06 | 0.03 | 0.00 | 0.09 | 0.06 | 0.00 | 0.05 |
|  | Resistance to skin deformation |  |  | 5 | 5 | 5 | 5 | 5 | 5 | 5 |

From Table 5, in view of the fact that the coating films 4-1 to 4-15 obtained in Examples 4-1 to 4-15 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

Preparation Examples 5-1 to 5-18

<Preparation of Liquid Composition I>

Each of the polymers C shown in Table 6 was dissolved in absolute ethanol as the solvent A; after confirming that the solution was transparent and free from a floating material and a precipitate, PARLEAM 3 was added as the solvent B; the contents were stirred and homogenized; and the resultant was filtered with a cellulose acetate syringe filter having a pore diameter of 0.20 μm, manufactured by Advantech Co., Ltd. There were thus obtained liquid compositions I5-1 to I5-18.

The dissolved amount of each of the polymers C used in Preparation Examples 5-1 to 5-18 in 100 g of the solvent B was less than 5 g, and the dissolved amount thereof in 100 g of the solvent A was 5 g or more.

Examples 5-1 to 5-18

<Formation of Coating Film>

Dried coating films 5-1 to 5-18 were obtained in the same manner as in Example 2-1, except for changing the liquid composition I1-1 to each of the liquid compositions as shown in Table 6.

Subsequently, the concealment, the resistance to skin deformation, and the FD adherence were evaluated in the same manners as mentioned above. The results are shown in Table 6.

TABLE 6

|  |  |  |  |  | Example | | | | | | | | |
|---|---|---|---|---|---|---|---|---|---|---|---|---|---|
|  |  |  |  |  | 5-1 | 5-2 | 5-3 | 5-4 | 5-5 | 5-6 | 5-7 | 5-8 | 5-9 |
| Step 1 | Liquid composition I No. |  |  |  | I5-1 | I5-2 | I5-3 | I5-4 | I5-5 | I5-6 | I5-7 | I5-8 | I5-9 |
|  | Composition (parts) | Solvent A |  | Ethanol | 70 | 70 | 70 | 70 | 70 | 70 | 70 | 70 | 70 |
|  |  | Solvent B |  | PARLEAM 3 | 20 | 20 | 20 | 20 | 20 | 20 | 20 | 20 | 20 |
|  |  | Polymer C | Anionic polymer CI | ULTRAHOLD 8 | 5 | 5 | 5 | 5 |  |  |  |  |  |
|  |  |  |  | ULTRAHOLD STRONG |  |  |  |  | 5 | 5 | 5 | 5 |  |
|  |  |  |  | ULTRAHOLD POWER-dry | 5 |  |  |  |  | 5 |  |  | 5 |

TABLE 6-continued

|  |  |  |  |  |  |  |  |  |  |  |  |
|---|---|---|---|---|---|---|---|---|---|---|---|
|  |  | Cationic polymer CII-1 | Cationic polymer 1 |  | 5 |  |  | 5 |  |  |  |
|  |  |  | Cationic polymer 2 |  |  | 5 |  |  |  |  |  |
|  |  | Cationic silicone polymer CII-2 | Cationic silicone polymer 1 |  |  |  |  |  |  | 5 |  |
|  |  |  | Cationic silicone polymer 2 |  |  |  |  |  |  |  | 5 |
|  |  |  | Cationic silicone polymer 3 |  |  |  | 5 |  |  | 5 |  |
|  |  | Betaine polymer CIII | YUKA FORMER SM-dry |  |  |  |  |  |  |  |  |
|  |  | Nonionic polymer | Polyvinyl butyral Polyurethanepolyurea |  |  |  |  |  |  |  |  |
|  | Viscosity of liquid composition I (mPa·s) |  |  | 12.2 | 48.2 | 16.2 | 6.6 | 14.8 | 23.1 | 9.2 | 10.1 | 17.5 |
|  | Base material |  |  |  |  |  |  | SUPPLALE |  |  |  |  |
|  | Wet film thickness T (μm) |  |  | 100 | 100 | 100 | 100 | 100 | 100 | 100 | 100 | 100 |
| Step 2 | Kind of atomizer |  |  | A | A | A | A | A | A | A | A | A |
|  | Atomizing time (sec) |  |  | 5 | 5 | 5 | 5 | 5 | 5 | 5 | 5 | 5 |
|  | Average particle diameter of atomized droplets (μm) |  |  |  |  |  |  | 1 to 5 |  |  |  |  |
| Evaluation | Coating film No. |  |  | 5-1 | 5-2 | 5-3 | 5-4 | 5-5 | 5-6 | 5-7 | 5-8 | 5-9 |
|  | Whiteness (image density) | Coating film |  | 0.60 | 0.67 | 0.58 | 0.48 | 0.50 | 0.55 | 0.53 | 0.58 | 0.42 |
|  |  | After FD coating |  | 0.30 | 0.30 | 0.30 | 0.30 | 0.30 | 0.30 | 0.30 | 0.30 | 0.30 |
|  |  | After FD scraping |  | 0.45 | 0.41 | 0.42 | 0.44 | 0.47 | 0.49 | 0.45 | 0.43 | 0.44 |
|  | Amount in change of image density before and after FD scraping |  |  | 0.15 | 0.11 | 0.12 | 0.14 | 0.17 | 0.19 | 0.15 | 0.13 | 0.14 |
|  | Resistance to skin deformation |  |  | 5 | 5 | 5 | 5 | 5 | 5 | 5 | 5 | 5 |

|  |  |  |  | Example |  |  |  |  |  |  |  |  |
|---|---|---|---|---|---|---|---|---|---|---|---|---|
|  |  |  |  | 5-10 | 5-11 | 5-12 | 5-13 | 5-14 | 5-15 | 5-16 | 5-17 | 5-18 |
| Step 1 | Liquid composition I No. |  |  | I5-10 | I5-11 | I5-12 | I5-13 | I5-14 | I5-15 | I5-16 | I5-17 | I5-18 |
|  | Composition (parts) | Solvent A |  | Ethanol | 70 | 70 | 70 | 70 | 70 | 70 | 70 | 70 | 70 |
|  |  | Solvent B |  | PARLEAM 3 | 20 | 20 | 20 | 20 | 20 | 20 | 20 | 20 | 20 |
|  |  | Polymer C | Anionic polymer CI | ULTRAHOLD 8 |  |  |  |  |  |  | 3 |  |  |
|  |  |  |  | ULTRAHOLD STRONG |  |  |  |  |  |  |  |  |  |
|  |  |  |  | ULTRAHOLD POWER-dry | 5 |  |  |  |  |  |  |  |  |
|  |  | Cationic polymer CII-1 | Cationic polymer 1 |  |  | 5 | 5 |  |  |  |  |  |  |
|  |  |  | Cationic polymer 2 |  |  |  |  | 5 | 5 | 5 |  |  |  |
|  |  | Cationic silicone polymer CII-2 | Cationic silicone polymer 1 |  |  |  |  |  | 5 |  |  |  |  |
|  |  |  | Cationic silicone polymer 2 |  |  | 5 |  |  |  | 5 |  |  |  |
|  |  |  | Cationic silicone polymer 3 |  | 5 |  | 5 |  |  | 5 | 3 |  |  |
|  |  | Betaine polymer CIII | YUKA FORMER SM-dry |  |  |  |  |  |  |  | 4 |  |  |
|  |  | Nonionic polymer | Polyvinyl butyral |  |  |  |  |  |  |  |  | 10 |  |
|  |  |  | Polyurethanepolyurea |  |  |  |  |  |  |  |  |  | 10 |
|  | Viscosity of liquid composition I (mPa·s) |  |  |  | 13.7 | 14.9 | 12.3 | 12.4 | 17.6 | 11.8 | 14.6 | 53.2 | 13.8 |
|  | Base material |  |  |  |  |  |  | SUPPLALE |  |  |  |  |  |
|  | Wet film thickness T (μm) |  |  |  | 100 | 100 | 100 | 100 | 100 | 100 | 101 | 102 | 103 |
| Step 2 | Kind of atomizer |  |  |  | A | A | A | A | A | A | A | A | A |
|  | Atomizing time (sec) |  |  |  | 5 | 5 | 5 | 5 | 5 | 5 | 5 | 5 | 5 |
|  | Average particle diameter of atomized droplets (μm) |  |  |  |  |  |  |  | 1 to 5 |  |  |  |  |
| Evaluation | Coating film No. |  |  |  | 5-10 | 5-11 | 5-12 | 5-13 | 5-14 | 5-15 | 5-16 | 5-17 | 5-18 |
|  | Whiteness (image density) | Coating film |  |  | 0.53 | 0.53 | 0.46 | 0.53 | 0.56 | 0.40 | 0.38 | 0.95 | 0.98 |
|  |  | After FD coating |  |  | 0.30 | 0.30 | 0.30 | 0.30 | 0.30 | 0.30 | 0.30 | 0.30 | 0.30 |
|  |  | After FD scraping |  |  | 0.46 | 0.40 | 0.39 | 0.39 | 0.40 | 0.40 | 0.35 | 0.88 | 0.78 |
|  | Amount in change of image density before and after FD scraping |  |  |  | 0.16 | 0.10 | 0.09 | 0.09 | 0.10 | 0.10 | 0.05 | 0.58 | 0.48 |
|  | Resistance to skin deformation |  |  |  | 5 | 5 | 5 | 5 | 5 | 5 | 5 | 3 | 3 |

From Table 6, in view of the fact that the coating films 5-1 to 5-18 obtained in Examples 5-1 to 5-18 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

Preparation Examples 6-1 to 6-10

<Preparation of Liquid Composition I>

Each of the polymers C shown in Table 7 was dissolved in absolute ethanol as the solvent A; after confirming that the solution was transparent and free from a floating material and a precipitate, the solvent B shown in Table 7 was added; the contents were stirred and homogenized; and the resultant was filtered with a cellulose acetate syringe filter having a pore diameter of 0.20 μm, manufactured by Advantech Co., Ltd. There were thus obtained liquid compositions I6-1 to I6-10.

The dissolved amount of each of the polymers C used in Preparation Examples 6-1 to 6-10 in 100 g of the solvent B was less than 5 g, and the dissolved amount thereof in 100 g of the solvent A was 5 g or more.

Examples 6-1 to 6-10

<Formation of Coating Film>

Dried coating films 6-1 to 6-10 were obtained in the same manner as in Example 2-1, except for changing the liquid composition I1-1 to each of the liquid compositions as shown in Table 7.

Subsequently, the concealment, the resistance to skin deformation, and the FD adherence were evaluated in the same manners as mentioned above. The results are shown in Table 7.

TABLE 7

|   |   |   |   |   |   | Example | | | | | |
|---|---|---|---|---|---|---|---|---|---|---|---|
|   |   |   |   |   |   | 6-1 | 6-2 | 6-3 | 6-4 | 6-5 | 6-6 |
| Step 1 | Liquid composition I No. |   |   |   |   | I6-1 | I6-2 | I6-3 | I6-4 | I6-5 | I6-6 |
|   | Composition (parts) | Solvent A | Ethanol (boiling point: 78° C., Ra: 24) |   |   | 84 | 82 | 80 | 75 | 70 | 65 |
|   |   | Solvent B | Kind | Boiling point (° C.) | Ra |   |   |   |   |   |   |
|   |   |   | PARLEAM 3 | 179 | 45 | 6 | 8 | 10 | 15 | 20 | 25 |
|   |   |   | PARLEAM 4 | 262 | 45 |   |   |   |   |   |   |
|   |   |   | KF-96A-1CS | 153 | 45 |   |   |   |   |   |   |
|   |   |   | TMF-1.5 | 191 | 45 |   |   |   |   |   |   |
|   |   | Polymer C | ULTRAHOLD 8 |   |   | 5 | 5 | 5 | 5 | 5 | 5 |
|   |   |   | Cationic silicone polymer 3 |   |   |   |   |   |   |   |   |
|   |   |   | RAM RESIN 2000-dry |   |   | 5 | 5 | 5 | 5 | 5 | 5 |
|   | Viscosity of liquid composition I (mPa · s) |   |   |   |   | 9.4 | 9.5 | 9.8 | 10.0 | 10.2 | 11.1 |
|   | Base material |   |   |   |   |   | | SUPPLALE | | | |
|   | Wet film thickness T (μm) |   |   |   |   | 100 | 100 | 100 | 100 | 100 | 100 |
| Step 2 | Kind of atomizer |   |   |   |   | A | A | A | A | A | A |
|   | Atomizing time (sec) |   |   |   |   | 5 | 5 | 5 | 5 | 5 | 5 |
|   | Average particle diameter of atomized droplets (μm) |   |   |   |   |   | | 1 to 5 | | | |
| Evaluation | Coating film No. |   |   |   |   | 6-1 | 6-2 | 6-3 | 6-4 | 6-5 | 6-6 |
|   | Whiteness (image density) | Coating film |   |   |   | 0.62 | 0.49 | 0.38 | 0.34 | 0.32 | 0.34 |
|   |   | After FD coating |   |   |   | 0.30 | 0.30 | 0.30 | 0.30 | 0.30 | 0.30 |
|   |   | After FD scraping |   |   |   | 0.41 | 0.35 | 0.32 | 0.31 | 0.30 | 0.30 |
|   | Amount in change of image density before and after FD scraping |   |   |   |   | 0.11 | 0.05 | 0.02 | 0.01 | 0.00 | 0.00 |
|   | Resistance to skin deformation |   |   |   |   | 5 | 5 | 5 | 5 | 5 | 5 |

|   |   |   |   |   |   | Example | | | |
|---|---|---|---|---|---|---|---|---|---|
|   |   |   |   |   |   | 6-7 | 6-8 | 6-9 | 6-10 |
| Step 1 | Liquid composition I No. |   |   |   |   | I6-7 | I6-8 | I6-9 | I6-10 |
|   | Composition (parts) | Solvent A | Ethanol (boiling point: 78° C., Ra: 24) |   |   | 60 | 70 | 84 | 84 |
|   |   | Solvent B | Kind | Boiling point (° C.) | Ra |   |   |   |   |
|   |   |   | PARLEAM 3 | 179 | 45 | 30 |   |   |   |
|   |   |   | PARLEAM 4 | 262 | 45 |   | 20 |   |   |
|   |   |   | KF-96A-1CS | 153 | 45 |   |   | 6 |   |
|   |   |   | TMF-1.5 | 191 | 45 |   |   |   | 6 |
|   |   | Polymer C | ULTRAHOLD 8 |   |   | 5 | 5 | 3 | 3 |
|   |   |   | Cationic silicone polymer 3 |   |   |   |   | 4 | 4 |
|   |   |   | RAM RESIN 2000-dry |   |   | 5 | 5 | 3 | 3 |
|   | Viscosity of liquid composition I (mPa · s) |   |   |   |   | 13.4 | 12.1 | 14.3 | 16.5 |
|   | Base material |   |   |   |   |   | SUPPLALE | | |
|   | Wet film thickness T (μm) |   |   |   |   | 100 | 100 | 100 | 100 |
| Step 2 | Kind of atomizer |   |   |   |   | A | A | A | A |
|   | Atomizing time (sec) |   |   |   |   | 5 | 5 | 5 | 5 |
|   | Average particle diameter of atomized droplets (μm) |   |   |   |   |   | 1 to 5 | | |
| Evaluation | Coating film No. |   |   |   |   | 6-7 | 6-8 | 6-9 | 6-10 |
|   | Whiteness (image | Coating film |   |   |   | 0.43 | 0.32 | 0.68 | 0.79 |
|   |   | After FD coating |   |   |   | 0.30 | 0.30 | 0.30 | 0.30 |

TABLE 7-continued

| | | | | | |
|---|---|---|---|---|---|
| density) | After FD scraping | 0.31 | 0.30 | 0.45 | 0.50 |
| | Amount in change of image density before and after FD scraping | 0.01 | 0.00 | 0.15 | 0.20 |
| | Resistance to skin deformation | 5 | 5 | 5 | 5 |

From Table 7, in view of the fact that the coating films 6-1 to 6-10 obtained in Examples 6-1 to 6-10 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

Example 7-1

<Formation of Coating Film>

A dried polymer coating film 7-1 was obtained in the same manner as in Example 2-1, except that the temperature and humidity conditions in the environmental chamber were changed to 25° C. for the temperature and to 10% for the humidity.

Subsequently, the concealment, the resistance to skin deformation, and the FD adherence were evaluated in the same manners as mentioned above. The results are shown in Table 8.

Examples 7-2 to 7-4

<Formation of Coating Film>

The step 1 and the step 2 were performed in the same manner as in Example 2-1, except that the temperature and humidity conditions in the environmental chamber were changed to 25° C. for the temperature and to 10% for the humidity.

Furthermore, as for the drying treatment, in Example 7-2, blast drying at a temperature of 25° C. was performed; in Example 7-3, warm air drying at a temperature of 60° C. was performed; and in Example 7-4, drying was performed while keeping the temperature within a thermos-hygrostat TH-412E, manufactured by Kusumoto Chemicals, Ltd., in which the temperature and humidity condition was regulated at a temperature of 35° C. and a humidity of 40%, and a windbreak was provided such that the circulating wind within the thermos-hygrostat did not strike the coating film surface. There were thus obtained dried polymer coating films 7-2 to 7-4.

Subsequently, the concealment, the resistance to skin deformation, and the FD adherence were evaluated in the same manners as mentioned above. The results are shown in Table 8.

<Evaluation of Whiteness Expression Speed>

In the evaluation of the whiteness, after applying ion-exchanged water, the whiteness was measured every minute, and a time necessary until the value of whiteness became stable was measured, thereby evaluating the whiteness expression speed. On the occasion of measuring the whiteness, at the point of time when a difference from the whiteness measured one minute ago became 0.1 or less was considered such that the whiteness became stable, and that time was recorded, whereby the whiteness on that occasion was evaluated. The results are shown in Table 8. As the time until the whiteness becomes stable is shorter, such is more preferred. The case where the time is 30 minutes or shorter is not practically problematic.

TABLE 8

| | | | | Example | | | |
|---|---|---|---|---|---|---|---|
| | | | | 7-1 | 7-2 | 7-3 | 7-4 |
| Step 1 | Liquid composition I No. | | | I1-1 | I1-1 | I1-1 | I1-1 |
| | Composition | Solvent A | Ethanol | 70 | 70 | 70 | 70 |
| | (parts) | Solvent B | PARLEAM 3 | 20 | 20 | 20 | 20 |
| | | Polymer C | ULTRAHOLD 8 | 5 | 5 | 5 | 5 |
| | | | RAM RESIN 2000-dry | 5 | 5 | 5 | 5 |
| | Viscosity of liquid composition I (mPa · s) | | | 10.2 | 10.2 | 10.2 | 10.2 |
| | Base material | | | | SUPPLALE | | |
| | Wet film thickness T (μm) | | | 100 | 100 | 100 | 100 |
| Step 2 | Kind of atomizer | | | A | A | A | A |
| | Atomizing time (sec) | | | 5 | 5 | 5 | 5 |
| | Average particle diameter of atomized droplets (μm) | | | | 1 to 5 | | |
| Drying treatment | | | | Natural drying | Blast drying | Warm air drying | Keeping warm at 35° C. |
| Evaluation | Coating film No. | | | 7-1 | 7-2 | 7-3 | 7-4 |
| | Whiteness expression speed [Time until the whiteness becomes stable (min)] | | | 10 | 1 | 1 | 1 |
| | Whiteness (image density) | | Coating film | 0.32 | 0.32 | 0.32 | 0.32 |
| | | | After FD coating | 0.30 | 0.30 | 0.30 | 0.30 |
| | | | After FD scraping | 0.30 | 0.30 | 0.30 | 0.30 |
| | Amount in change of image density before and after FD scraping | | | 0.00 | 0.00 | 0.00 | 0.00 |
| | Resistance to skin deformation | | | 5 | 5 | 5 | 5 |

From Table 8, in view of the fact that the coating films 7-1 to 7-4 obtained in Examples 7-1 to 7-4 are high in the whiteness, exhibit high concealment even without containing an inorganic pigment, and are excellent in the resistance to skin deformation, and therefore, it is noted that they are excellent in the makeup durability. Furthermore, even in the case of being scraped after the FD coating, it is noted that these coating films are able to keep the high whiteness and are also excellent in the FD adherence.

INDUSTRIAL APPLICABILITY

In accordance with the present invention, even when an inorganic pigment is not used, it is possible to form a coating film which has a high whiteness, is excellent in the concealment, and has excellent makeup durability such that the markup deterioration is hardly caused.

REFERENCE SIGNS LIST

11: Inorganic particles
12, 22: Coating film
13, 23: Skin
14, 24: Sulcus cutis
15, 25: Crista cutis
21: Primary particles

The invention claimed is:

1. A method for forming a coating film, the method comprising:
   coating a liquid composition I comprising a solvent A, a solvent B, and a polymer C to a skin,
   wherein:
   a boiling point of the solvent A is lower than 99° C., and a distance Ra of the Hansen solubility parameter of the solvent A to water as expressed by the following equation (1) is 36 or less,
   a boiling point of the solvent B is 150° C. or higher, and a distance Ra of the Hansen solubility parameter of the solvent B to water as expressed by the following equation (1) is 40 or more,
   the solvent B contains at least one member selected from the group consisting of a hydrocarbon oil and a silicone oil,
   the solvent B is compatible with the solvent A,
   the polymer C is soluble in the solvent A but insoluble in the solvent B,
   a content of the solvent A in the liquid composition I is 50% by mass or more and 90% by mass or less,
   a content of the solvent B in the liquid composition I is 5% by mass or more and 40% by mass or less,
   a content of the polymer C in the liquid composition I is 2% by mass or more and 20% by mass or less, $$Ra = (4 \times \Delta D^2 + \Delta P^2 + \Delta H^2)^{0.5} \quad (1)$$

wherein,
$\Delta D$ is a difference of dispersing component in the Hansen solubility parameter between a solvent and water,
$\Delta P$ is a difference of polar component in the Hansen solubility parameter between a solvent and water, and
$\Delta H$ is a difference of hydrogen-binding component in the Hansen solubility parameter between a solvent and water,
the coating film comprises primary particles that are formed following drying of the liquid composition I coated on the skin,
the primary particles having a core-shell structure in which the solvent B constitutes the core, and the polymer C constitutes the shell, and an average particle diameter of the primary particles is 0.1 μm or more and 5 μm or less, and
the primary particles are adsorbed to each other at a plurality of positions through the shell.

2. The method for forming a coating film according to claim 1, wherein the method further comprises applying droplets of a liquid II comprising water to the liquid composition I on the skin.

3. The method for forming a coating film according to claim 2, wherein a content of water in the liquid II comprising water is 50% by mass or more.

4. The method for forming a coating film according to claim 2, wherein the method for applying droplets comprises atomizing the droplets with an atomizer.

5. The method for forming a coating film according to claim 1, wherein the solvent A is at least one selected from the group consisting of ethanol, propanol, isopropanol, and tert-butyl alcohol.

6. The method for forming a coating film according to claim 1, wherein the solvent B comprises 50% by mass or more of at least one selected from the group consisting of a hydrocarbon oil and a silicone oil each having a weight average molecular weight of 150 or more and 1,000 or less.

7. The method for forming a coating film according to claim 1, wherein the polymer C is an ionic polymer.

8. The method for forming a coating film according to claim 1, wherein the polymer C comprises, as a monomer constitutional unit, at least one selected from the group consisting of a monomer having an acidic group, a monomer having a basic group, and a betaine monomer.

9. The method for forming a coating film according to claim 1, wherein the polymer C comprises an anionic polymer CI comprising a constitutional unit derived from a monomer having an acidic group; and at least one selected from the group consisting of a cationic polymer CII-1 comprising a constitutional unit derived from a monomer having a basic group, a cationic silicone polymer CII-2, and a betaine polymer CIII comprising a constitutional unit derived from a betaine monomer.

10. The method for forming a coating film according to claim 1, wherein the polymer C comprises an anionic polymer CI comprising a constitutional unit derived from a monomer having an acidic group; and a betaine polymer CIII comprising a constitutional unit derived from a betaine monomer.

11. The method for forming a coating film according to claim 8, wherein the betaine monomer is at least one selected from the group consisting of a carboxybetaine monomer, a sulfobetaine monomer, and a phosphobetaine monomer.

12. The method for forming a coating film according to claim 1, wherein a viscosity at 20° C. of the liquid composition I is 1 mPa's or more and 300 mPa's or less.

13. The method for forming a coating film according to claim 1, wherein the coating film is a makeup coating film.

14. The method for forming a coating film according to claim 1, wherein the coating film is a coating film for protection of the skin.

15. The method for forming a coating film according to claim 1, wherein a mass ratio of the content of the polymer C to the total content of the solvent A and the solvent B in the liquid composition I [(polymer C)/{(solvent A)+(solvent B)}] is 0.01 or more and 1 or less.

16. The method for forming a coating film according to claim 1, wherein a content of an inorganic pigment in the liquid composition I is 10% by mass or less.

17. The method for forming a coating film according to claim 2, wherein an applied amount of the droplets is 0.01 mg/cm$^2$ or more and 10 mg/cm$^2$ or less.

18. The method for forming a coating film according to claim 2, wherein an average diameter of the droplets is 0.01 µm or more and 50 µm or less.

19. The method for forming a coating film according to claim 9, wherein a total content of the anionic polymer CI, the cationic polymer CII-1, the cationic silicone polymer CII-2, and the betaine polymer CIII in the polymer C is 60% by mass or more and 100% by mass or less.

20. The method for forming a coating film according to claim 1, wherein the polymer C contains at least one selected from the group consisting of an anionic polymer CI, a cationic polymer CII-1, a cationic silicone polymer CII-2, a betaine polymer CIII, and a nonionic polymer,
- the anionic polymer CI is a copolymer comprising a constitutional unit derived from a monomer having an acidic group, a constitutional unit derived from the hydrophobic group, and a constitutional unit derived from the nonionic monomer,
- the cationic polymer CII-1 is a copolymer comprising a constitutional unit derived from a monomer having a basic group, a constitutional unit derived from the hydrophobic group, and a constitutional unit derived from the nonionic monomer,
- the betaine polymer CIII is an N-methacryloyloxyethyl-N,N-dimethylammonium-α-N-methylcarboxybetaine/ methacrylic acid alkyl ester copolymer, and
- the nonionic polymer is at least one selected from the group consisting of polyvinyl acetal and polyurethane-polyurea.

* * * * *